(12) United States Patent
Birmingham et al.

(10) Patent No.: US 12,364,593 B2
(45) Date of Patent: *Jul. 22, 2025

(54) VALVE PROSTHESES HAVING AN INTEGRAL CENTERING MECHANISM AND METHODS OF USE THEREOF

(71) Applicant: MEDTRONIC VASCULAR, INC., Santa Rosa, CA (US)

(72) Inventors: Evelyn Birmingham, Ballybrit (IE); Bernard Mulvihill, Ballybrit (IE); Joel Racchini, Edina, MN (US); Jeffrey Sandstrom, Scandia, MN (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 150 days.

This patent is subject to a terminal disclaimer.

(21) Appl. No.: 18/331,419

(22) Filed: Jun. 8, 2023

(65) Prior Publication Data

US 2023/0310148 A1    Oct. 5, 2023

Related U.S. Application Data

(60) Continuation of application No. 16/811,255, filed on Mar. 6, 2020, now Pat. No. 11,723,764, which is a
(Continued)

(51) Int. Cl.
*A61F 2/24* (2006.01)
*A61F 2/844* (2013.01)
(Continued)

(52) U.S. Cl.
CPC .......... *A61F 2/2409* (2013.01); *A61F 2/2418* (2013.01); *A61F 2/844* (2013.01);
(Continued)

(58) Field of Classification Search
CPC ........ A61F 2/2418; A61F 2/2409; A61F 2/24; A61F 2/844; A61F 2/848
See application file for complete search history.

(56) References Cited

U.S. PATENT DOCUMENTS 4,909,252 A    3/1990  Goldberger
5,840,067 A   11/1998  Berguer et al.
(Continued)

OTHER PUBLICATIONS

The International Search Report and The Written Opinion of the International Searching Authority issued in International Application No. PCT/US2016/015157, dated Apr. 26, 2016.

*Primary Examiner* — Alvin J Stewart
(74) *Attorney, Agent, or Firm* — MEDLER FERRO WOODHOUSE & MILLS PLLC

(57) ABSTRACT

A transcatheter valve prosthesis including a tubular stent, a prosthetic valve component disposed within and secured to the stent, and a centering mechanism coupled to and encircling an outer surface of the tubular stent. The centering mechanism includes a self-expanding centering ring having an expanded diameter in the expanded configuration that is greater than an expanded diameter of the tubular stent in the expanded configuration and a plurality of self-expanding spokes radially extending between the tubular stent and the centering ring. The centering mechanism may include a base ring and/or a skirt. Alternatively, the centering mechanism includes a plurality of self-expanding loops. When each loop is in a delivery configuration the loop has a straightened profile that proximally extends from a proximal end of the tubular stent. When each loop is in an expanded configuration the loop has a U-shaped profile radially spaced apart from the tubular stent.

19 Claims, 21 Drawing Sheets

Related U.S. Application Data division of application No. 16/288,209, filed on Feb. 28, 2019, now Pat. No. 10,617,518, which is a division of application No. 15/000,513, filed on Jan. 19, 2016, now Pat. No. 10,231,827.

(60) Provisional application No. 62/134,754, filed on Mar. 18, 2015.

(51) Int. Cl.
*A61F 2/848* (2013.01)
*A61F 2/90* (2013.01)

(52) U.S. Cl.
CPC ............... *A61F 2/848* (2013.01); *A61F 2/90* (2013.01); *A61F 2220/0008* (2013.01); *A61F 2230/0013* (2013.01); *A61F 2230/0067* (2013.01)

(56) References Cited

U.S. PATENT DOCUMENTS

| Patent/Pub. No. | Date | Inventor |
|---|---|---|
| 6,629,534 B1 | 10/2003 | Goar et al. |
| 8,142,492 B2 | 3/2012 | Forster et al. |
| 8,454,686 B2 | 6/2013 | Alkhatib |
| 8,715,337 B2 | 5/2014 | Chuter |
| 8,926,690 B2 | 1/2015 | Kovalsky |
| 8,961,595 B2 | 2/2015 | Alkhatib |
| 9,017,399 B2 | 4/2015 | Gross et al. |
| 9,603,705 B2 | 3/2017 | Alkhatib |
| 9,681,951 B2 * | 6/2017 | Ratz .................... A61F 2/2418 |
| 10,231,827 B2 * | 3/2019 | Mulvihill ................ A61F 2/848 |
| 11,406,497 B2 | 8/2022 | Zhang et al. |
| 2004/0003819 A1 | 1/2004 | Goar et al. |
| 2004/0225354 A1 | 11/2004 | Allen et al. |
| 2005/0137699 A1 | 6/2005 | Salahieh et al. |
| 2006/0058871 A1 | 3/2006 | Zakay et al. |
| 2007/0088431 A1 | 4/2007 | Bourang et al. |
| 2007/0288087 A1 | 12/2007 | Fearnot et al. |
| 2008/0009746 A1 | 1/2008 | Forster et al. |
| 2008/0147160 A1 | 6/2008 | Ghione et al. |
| 2008/0221384 A1 | 9/2008 | Chi Sing et al. |
| 2009/0187241 A1 | 7/2009 | Melsheimer |
| 2010/0249915 A1 | 9/2010 | Zhang |
| 2010/0256723 A1 | 10/2010 | Murray |
| 2010/0280589 A1 | 11/2010 | Styrc |
| 2011/0125258 A1 | 5/2011 | Centola |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251681 A1 | 10/2011 | Shipley et al. |
| 2011/0251682 A1 | 10/2011 | Murray, III et al. |
| 2011/0264200 A1 | 10/2011 | Tran et al. |
| 2011/0264202 A1 | 10/2011 | Murray, III et al. |
| 2012/0078347 A1 | 3/2012 | Braido et al. |
| 2012/0209375 A1 | 8/2012 | Madrid et al. |
| 2013/0166022 A1 | 6/2013 | Conklin |
| 2013/0178931 A1 | 7/2013 | Fargahi |
| 2013/0190861 A1 | 7/2013 | Chau et al. |
| 2013/0304200 A1 | 11/2013 | McLean et al. |
| 2013/0310928 A1 | 11/2013 | Morriss et al. |
| 2013/0331929 A1 | 12/2013 | Mitra et al. |
| 2014/0018912 A1 | 1/2014 | Delaloye et al. |
| 2014/0046426 A1 | 2/2014 | Kovalsky |
| 2014/0067048 A1 | 3/2014 | Chau et al. |
| 2014/0194981 A1 | 7/2014 | Menk et al. |
| 2014/0194982 A1 | 7/2014 | Kovalsky et al. |
| 2014/0214157 A1 | 7/2014 | Bortlein et al. |
| 2014/0257248 A1 | 9/2014 | Millett |
| 2014/0277419 A1 | 9/2014 | Garde et al. |
| 2014/0371844 A1 | 12/2014 | Dale et al. |
| 2014/0379074 A1 | 12/2014 | Spence et al. |
| 2015/0018944 A1 | 1/2015 | O'Connell et al. |
| 2015/0209136 A1 | 7/2015 | Braido et al. |
| 2015/0238313 A1 | 8/2015 | Spence et al. |
| 2015/0257885 A1 | 9/2015 | McGuckin, Jr. |
| 2015/0351904 A1 | 12/2015 | Cooper et al. |
| 2016/0074164 A1 | 3/2016 | Naor |
| 2016/0242905 A1 | 8/2016 | Chambers |
| 2016/0361161 A1 | 12/2016 | Braido et al. |
| 2017/0128199 A1 | 5/2017 | Gurovich et al. |
| 2017/0156859 A1 | 6/2017 | Chang et al. |
| 2017/0189180 A1 | 7/2017 | Alkhatib |
| 2017/0189181 A1 | 7/2017 | Alkhatib et al. |
| 2017/0209261 A1 | 7/2017 | Börtlein et al. |
| 2017/0252154 A1 | 9/2017 | Tubishevitz et al. |
| 2017/0290661 A1 | 10/2017 | Von Segesser et al. |
| 2017/0340438 A1 | 11/2017 | Salahieh et al. |
| 2018/0125651 A1 | 5/2018 | Nasr |
| 2018/0333259 A1 * | 11/2018 | Dibie .................... A61F 2/2418 |
| 2018/0344457 A1 | 12/2018 | Gross et al. |
| 2019/0175338 A1 * | 6/2019 | White .................... A61F 2/2409 |
| 2019/0282364 A1 | 9/2019 | Khairkhahan et al. |
| 2019/0321171 A1 * | 10/2019 | Morriss ................ A61F 2/2436 |
| 2021/0307900 A1 | 10/2021 | Hacohen |
| 2022/0015900 A1 | 1/2022 | Agian et al. |
| 2022/0265422 A1 | 8/2022 | Sandquist et al. |

\* cited by examiner

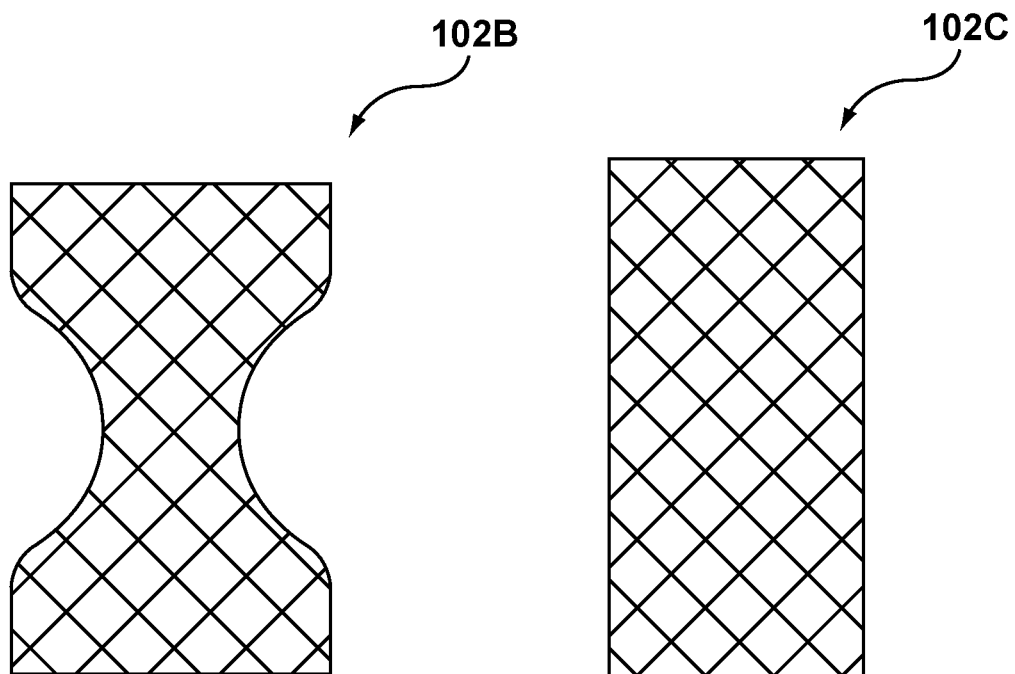
FIG. 1B  FIG. 1C

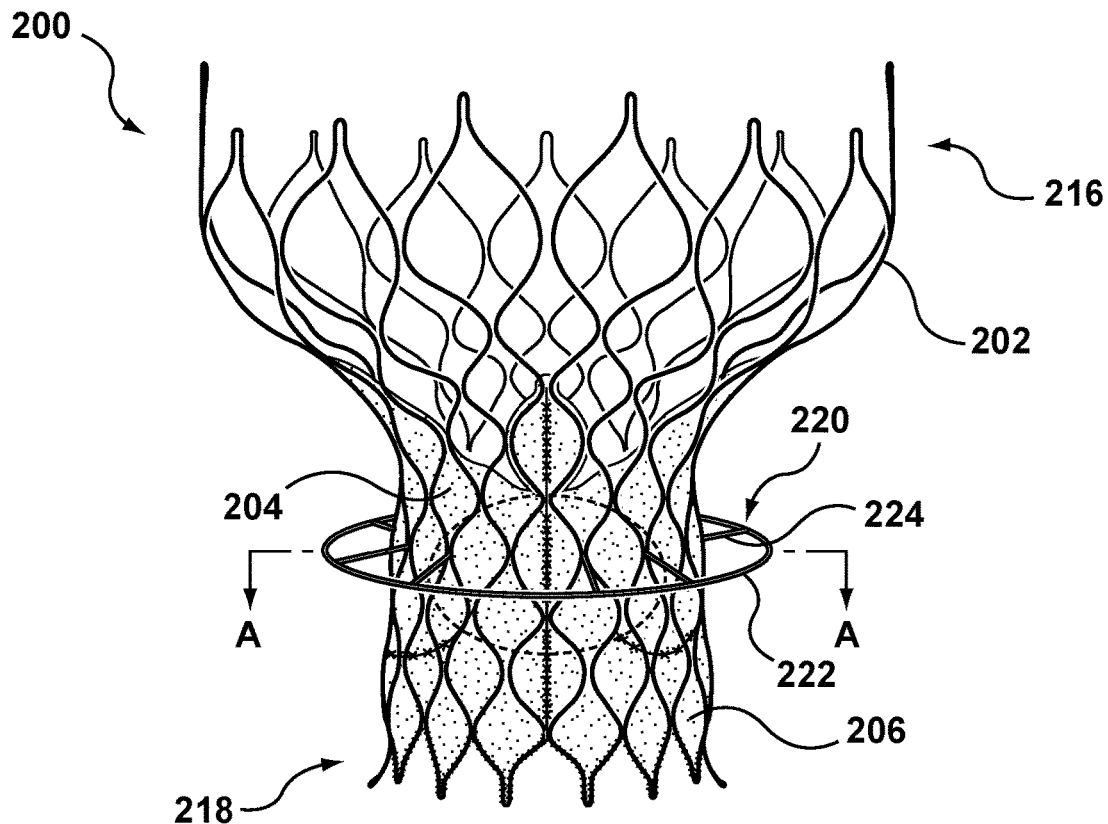
FIG. 2
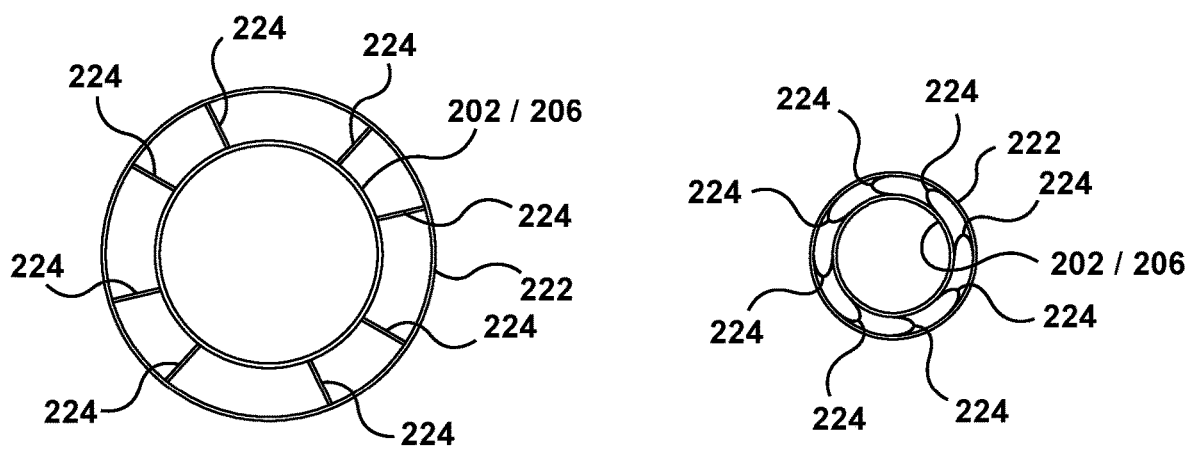
FIG. 2A  FIG. 3

United States Patent US 12,364,593 B2

VALVE PROSTHESES HAVING AN INTEGRAL CENTERING MECHANISM AND METHODS OF USE THEREOF

CROSS-REFERENCE TO RELATED APPLICATIONS

This application is a continuation of U.S. application Ser. No. 16/811,255, filed Mar. 6, 2020, which is a divisional of U.S. application Ser. No. 16/288,209, filed on Feb. 28, 2019, which is a divisional of U.S. application Ser. No. 15/000,513, filed on Jan. 19, 2016, which claims the benefit of U.S. Appl. No. 62/134,754, filed Mar. 18, 2015, each of which is hereby incorporated by reference in its entirety for all purposes.

FIELD OF THE INVENTION

The invention relates to valve prostheses and more particularly to a valve prosthesis having an integral centering mechanism for positioning the valve prosthesis in situ.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent or scaffold structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by compressing onto a balloon catheter or by being contained within a sheath component of a delivery system, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Pat. No. 8,721,713, both filed by Tower et al., each of which is incorporated by reference herein in its entirety.

Although transcatheter delivery methods have provided safer and less invasive methods for replacing a defective native heart valve, complications may arise including vessel trauma due to percutaneous delivery within highly curved anatomy and/or due to a large delivery profile of the prosthesis, inaccurate placement of the valve prosthesis, conduction disturbances, coronary artery obstruction, and/or undesirable paravalvular leakage and/or regurgitation at the implantation site. More particularly, for example, a prosthesis that is positioned too deep relative to the native annulus or placed unevenly within the native annulus in terms of depth may cause conduction disturbances. In another example, if a prosthesis is not circumferentially centered relative to the native annulus, the deployed prosthesis may dislodge from the implantation site and/or undesirable paravalvular leakage and/or regurgitation may occur. Thus, it is imperative that the prosthesis be accurately located relative to the native annulus prior to full deployment of the prosthesis.

Embodiments hereof are directed to a transcatheter valve prosthesis having an integral centering mechanism for positioning the valve prosthesis in situ to address one or more of the afore-mentioned complications.

BRIEF SUMMARY OF THE INVENTION

Embodiments hereof relate to a transcatheter valve prosthesis including a tubular stent having a compressed configuration for delivery within a vasculature and an expanded configuration for deployment within a native heart valve, a prosthetic valve component disposed within and secured to the stent, and a centering mechanism coupled to and encircling an outer surface of the tubular stent. The centering mechanism has a compressed configuration for delivery within a vasculature and an expanded configuration for deployment within a native heart valve. The centering mechanism includes a self-expanding centering ring having an expanded diameter in the expanded configuration that is greater than an expanded diameter of the tubular stent in the expanded configuration and a plurality of self-expanding spokes radially extending between the tubular stent and the centering ring.

In another embodiment hereof, a transcatheter valve prosthesis includes a tubular stent having a compressed configuration for delivery within a vasculature and an expanded configuration for deployment within a native heart valve, a prosthetic valve component disposed within and secured to the stent, and a plurality of self-expanding loops. A first end of each loop is fixed to a proximal end of the tubular stent and a second end of each loop is slidingly coupled to the proximal end of the tubular stent, the first end of the loop being circumferentially spaced apart from the second end of the loop. When each loop is in the delivery configuration the loop has a straightened profile that proximally extends from the proximal end of the tubular stent. When each loop is in the expanded configuration the loop has a U-shaped profile radially spaced apart from an outer surface of the tubular stent.

Embodiments hereof also relate to methods of delivering a valve prosthesis configured for implantation within a native valve annulus. A valve delivery system having a valve prosthesis mounted thereon is percutaneously introduced into the vasculature in a delivery configuration. The valve prosthesis includes a tubular stent, a prosthetic valve component disposed within and secured to the stent, and a centering mechanism coupled to and encircling an outer surface of the tubular stent. The centering mechanism includes a self-expanding centering ring and a plurality of self-expanding spokes radially extending between the tubular stent and the centering ring. The valve delivery system is tracked through the vasculature until the valve prosthesis is positioned within the native valve annulus. At least an inflow end of the tubular stent is deployed into an expanded configuration. The tubular stent has an expanded diameter in the expanded configuration. The centering mechanism of the valve prosthesis is deployed into an expanded configuration. The centering mechanism has an expanded diameter that is greater than the expanded diameter of the tubular stent in the expanded configuration. The valve delivery system is manipulated in order to catch the deployed centering mechanism onto the native valve annulus, thereby longitudinally centering the valve prosthesis within the native valve annulus. An outflow end of the tubular stent is deployed into the expanded configuration.

Embodiments hereof also relate to methods of delivering a valve prosthesis configured for implantation within a native valve annulus. A valve delivery system having a valve prosthesis mounted thereon is percutaneously introduced into the vasculature in a delivery configuration. The valve prosthesis includes a tubular stent, a prosthetic valve component disposed within and secured to the stent, and a centering mechanism coupled to and encircling an outer surface of the tubular stent. The centering mechanism includes a self-expanding centering ring and a plurality of self-expanding spokes radially extending between the tubular stent and the centering ring. The valve delivery system is tracked through the vasculature until the valve prosthesis is positioned within the native valve annulus. The centering mechanism of the valve prosthesis is deployed into an expanded configuration. The centering mechanism has an expanded diameter that is greater than the expanded diameter of the tubular stent in the expanded configuration and the centering mechanism catches onto the native valve annulus so as to be circumferentially and longitudinally centered within the native valve annulus. The tubular stent is deployed into an expanded configuration after deployment of the centering mechanism. The expanded diameter of the deployed centering mechanism is greater than an expanded diameter of the tubular stent in the expanded configuration and the deployed centering mechanism pulls the tubular stent into a circumferentially and longitudinally centered position within the native valve annulus.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1B is a side view illustration of an alternative configuration of a valve prosthesis for use in embodiments hereof.

FIG. 1C is a side view illustration of an alternative configuration of a valve prosthesis for use in embodiments hereof.

FIG. 2 is a side view illustration of a transcatheter valve prosthesis having an integral centering mechanism according to an embodiment hereof, wherein the valve prosthesis and the centering mechanism are in expanded or deployed configurations.

FIG. 2A is a cross-sectional view taken along line A-A of FIG. 2.

FIG. 3 is a cross-sectional view taken along line A-A of FIG. 2, wherein the valve prosthesis and the centering mechanism are in compressed or delivery configurations.

DETAILED DESCRIPTION OF THE INVENTION

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or scaffold structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorbornene, trans-polyisoprene, styrene-butadiene, and polyurethane. As well poly L-D lactic copolymer, oligo caprylactone copolymer and polycyclooctene can be used separately or in conjunction with other shape memory polymers. The term "substantially straight" and/or "straightened" is used in the following description and is intended to convey that the structures are linearly shaped or formed as a line within a tolerance of 5%.

The following detailed description is merely exemplary in nature and is not intended to limit the invention or the application and uses of the invention. Although the description of embodiments hereof are in the context of a transcatheter valve prosthesis within a native aortic valve, the valve prostheses of the invention can also be used in other areas of the body, such as within a native mitral valve, within a native pulmonic valve, within a native tricuspid valve, within a venous valve, or within a failed previously-implanted prosthesis. Furthermore, there is no intention to be bound by any expressed or implied theory presented in the preceding technical field, background, brief summary or the following detailed description.

Figure 1:
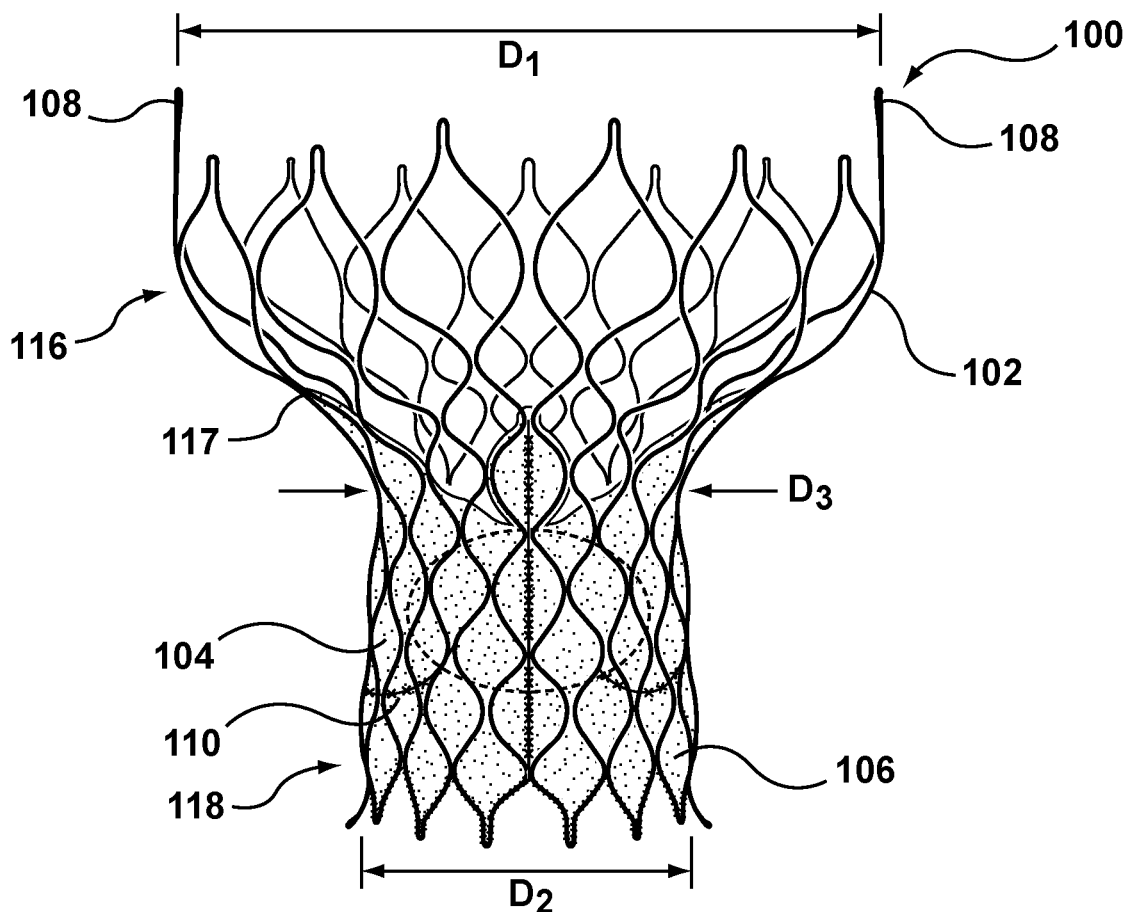
FIG. 1 is a side view illustration of an exemplary transcatheter valve prosthesis for use in embodiments hereof.

FIG. 1 depicts an exemplary transcatheter valve prosthesis 100. Valve prosthesis 100 is illustrated herein in order to facilitate description of the methods and components utilized to longitudinally and/or circumferentially center the prosthesis according to embodiments hereof. It is understood that any number of alternate heart valve prostheses can be used with the methods and devices described herein. Valve prosthesis 100 is merely exemplary and is described in more detail in U.S. Patent Application Pub. No. 2011/0172765 to Nguyen et al., which is herein incorporated by reference in its entirety. Other non-limiting examples of transcatheter valve prostheses are described in U.S. Pat. Appl. Pub. No. 2006/0265056 to Nguyen et al., U.S. Pat. Appl. Pub. No. 2007/0239266 to Birdsall, U.S. Pat. Appl. Pub. No. 2007/0239269 to Dolan et al., and U.S. Pat. Appl. Pub. No. 2008/0071361 to Tuval et al., each of which is incorporated by reference herein in its entirety.

Valve prosthesis 100 includes an expandable stent or frame 102 that supports a prosthetic valve component within the interior of stent 102. In embodiments hereof, stent 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. Alternatively, valve prosthesis 100 may be balloon-expandable as would be understood by one of ordinary skill in the art.

Figure 1A:
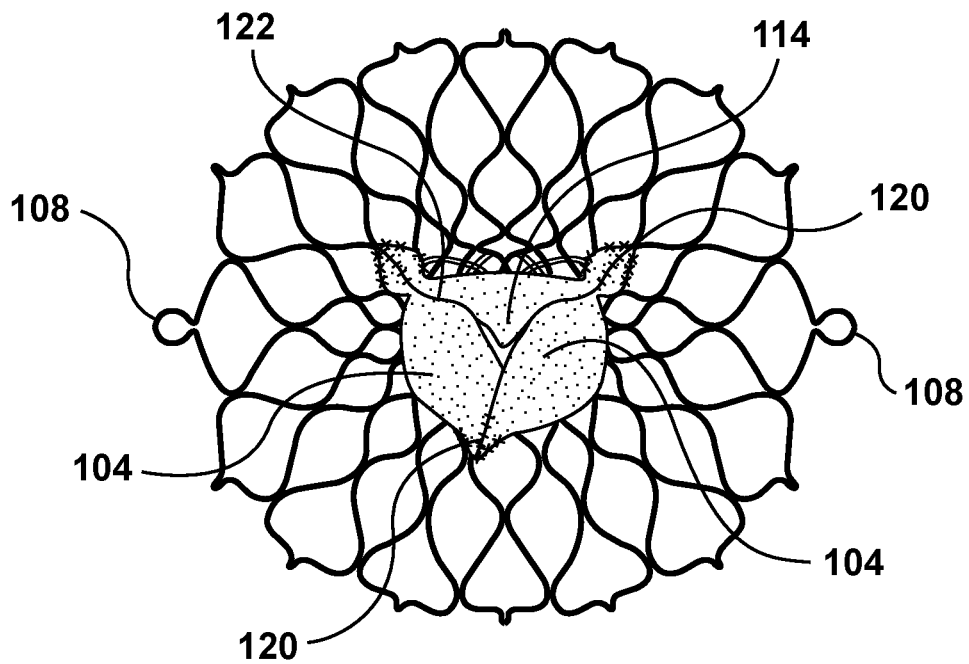
FIG. 1A is a top view illustration of the valve prosthesis of FIG. 1.

In the embodiment depicted in FIGS. 1 and 1A, stent 102 of valve prosthesis 100 has a deployed configuration including an enlarged or flared first end or section 116, a constriction or waist region 117, and a second end or section 118. Enlarged first section 116 has nominal deployed diameter $D_1$, second section 118 has nominal deployed diameter $D_2$, and constriction region 117 has deployed substantially fixed diameter $D_3$. Each section of stent 102 may be designed with a number of different configurations and sizes to meet the different requirements of the location in which it may be implanted. When configured as a replacement for an aortic valve, second section 118 functions as an inflow end of valve prosthesis 100 and extends into and anchors within the aortic annulus of a patient's left ventricle, while first section 116 functions as an outflow end of valve prosthesis 100 and is positioned in the patient's ascending aorta. When configured as a replacement for a mitral valve, enlarged or flared first section 116 functions as an inflow end of valve prosthesis 100 and is positioned in the patient's left atrium, while second section 118 functions as an outflow end of valve prosthesis 100 and extends into and anchors within the mitral annulus of a patient's left ventricle. For example, U.S. Patent Application Publication Nos. 2012/0101572 to Kovalsky et al. and 2012/0035722 to Tuval, each of which are herein incorporated by reference in their entirety, illustrate heart valve prostheses configured for placement in a mitral valve. Each section of stent 102 may have the same or different cross-section which may be for example circular, ellipsoidal, rectangular, hexagonal, rectangular, square, or other polygonal shape, although at present it is believed that circular or ellipsoidal may be preferable when the valve prosthesis is being provided for replacement of the aortic or mitral valve. As alternatives to the deployed configuration of FIGS. 1 and 1A, the stent/valve support frame may have an hourglass configuration 102B shown in FIG. 1B, a generally tubular configuration 102C as shown in FIG. 1C, or other stent configuration or shape known in the art for valve replacement. Stent 102 also may include eyelets 108 that extend from first end 116 thereof for use in loading the valve prosthesis 100 into a delivery catheter (not shown).

As previously mentioned, valve prosthesis 100 includes a prosthetic valve component within the interior of stent 102. The prosthetic valve component is capable of blocking flow in one direction to regulate flow there through via valve leaflets 104 that may form a bicuspid or tricuspid replacement valve. FIG. 1A is an end view of FIG. 1 and illustrates an exemplary tricuspid valve having three leaflets 104, although a bicuspid leaflet configuration may alternatively be used in embodiments hereof. More particularly, if valve prosthesis 100 is configured for placement within a native valve having three leaflets such as the aortic, tricuspid, or pulmonary valves, valve prosthesis 100 includes three valve leaflets 104. If valve prosthesis 100 is configured for placement within a native valve having two leaflets such as the mitral valve, valve prosthesis 100 includes two valve leaflets 104. Valve leaflets 104 are sutured or otherwise securely and sealingly attached to the interior surface of stent 102 and/or graft material 106 which encloses or lines a portion of stent 102 as would be known to one of ordinary skill in the art of prosthetic tissue valve construction. Referring to FIG. 1, leaflets 104 are attached along their bases 110 to graft material 106, for example, using sutures or a suitable biocompatible adhesive. Adjoining pairs of leaflets are attached to one another at their lateral ends to form commissures 120, with free edges 122 of the leaflets forming coaptation edges that meet in area of coaptation 114.

Leaflets 104 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 104 include DACRON® polyester commercially available from Invista North America S.A.R.L. of Wilmington, DE, other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 106 may also be a natural or biological material such as pericardium or another membranous tissue such as intestinal submucosa. Alternatively, graft material 106 may be a low-porosity woven fabric, such as polyester, Dacron fabric, or PTFE, which creates a one-way fluid passage when attached to the stent. In one embodiment, graft material 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In one embodiment shown in FIG. 1, graft material 106 extends from leaflets bases 110 to second end 118 of valve prosthesis.

As previously described herein, proper positioning of a transcatheter valve prosthesis is required in order to successfully implant the valve prosthesis within a native valve annulus. If the prosthesis is incorrectly positioned relative to the native valve annulus, the deployed device can leak and dislodge from the implantation site. Embodiments hereof are directed to a transcatheter valve prosthesis having an integral centering mechanism for positioning the valve prosthesis in situ such that the valve prosthesis is longitudinally and/or circumferentially centered in a native valve annulus at the target implantation site, such as for example a native aortic valve. As used herein, "circumferentially centered" and/or "circumferentially center" include a prosthesis that is placed or situated in the center of a body lumen such that a centerpoint of the prosthesis is equidistant to the vessel wall of the body lumen within a tolerance of 10% of the mean lumen diameter of the body lumen. As used herein, "lumen diameter" for a circular body lumen is the diameter of the circular lumen, "lumen diameter" for an eccentric or non-circular body lumen is the diameter of a circular lumen with an equivalent perimeter length, and "lumen diameter" for an oval body lumen is the average of the major and minor diameters of the oval lumen. As used herein, "longitudinally centered" and/or "longitudinally center" include a valve prosthesis having a distal end that is positioned or implanted between 0 mm and 6 mm distal to the native valve annulus within a tolerance of +/−2 mm. The longitudinal centering devices described herein prevent the valve prosthesis from being implanted too deep or too shallow into the left ventricle relative to the native annulus. The circumferential and/or longitudinal centering devices described herein serve to eliminate or minimize canting of an implanted valve prosthesis, or stated another way, serve to position a valve prosthesis in situ such that after implantation thereof the valve plane of the valve prosthesis is substantially (i.e., within the tolerances stated above) parallel to the valve plane of the native valve.

More particularly, FIG. 2 is a side view of a transcatheter valve prosthesis 200 according to an embodiment hereof. Similar to transcatheter valve prosthesis 100, transcatheter valve prosthesis 200 includes a tubular stent 202 having a compressed configuration for delivery within a vasculature and an expanded configuration for deployment within a native heart valve and a prosthetic valve component including leaflets 204 disposed within and secured to stent 202. Stent 202 includes a first end 216 and a second end 218, and graft material 206 encloses or lines a portion of stent 202. Valve prosthesis 200 also includes a centering mechanism 220 coupled to and encircling an outer surface of tubular stent 202. Centering mechanism 220 includes a self-expanding centering ring 222 and a plurality of spokes 224 radially extending between tubular stent 202 and centering ring 222. Centering mechanism 220 has a compressed configuration for delivery within a vasculature, as will be described in more detail herein with respect to FIG. 3, and an expanded configuration for deployment within a native heart valve. Centering mechanism 220 and stent 202 are shown in their expanded configurations in FIG. 2. In their expanded configurations, centering ring 222 has an expanded diameter that is greater than an expanded diameter of tubular stent 202 such that centering ring 222 is radially spaced apart from the outer surface of tubular stent 202.

When deployed, centering ring 222 is configured to abut against an abutment surface defined by a native valve annulus to longitudinally center valve prosthesis 200 within the native valve annulus. More particularly, as will be described in more detail with reference to FIG. 7, centering ring 222 is configured to be initially positioned in situ slightly above the abutment surface defined by the native valve annulus. Valve prosthesis 200, including centering mechanism 220, is then translated or moved such that centering ring 222 contacts or abuts against the abutment surface of the native valve annulus. As such, centering ring 222 is utilized as a depth marker or reference point to longitudinally center valve prosthesis 200 by preventing the valve prosthesis from being positioned too deep or too shallow within the left ventricle.

FIG. 2A is a cross-sectional view taken along line A-A of FIG. 2, with leaflets 204 removed for sake of illustration only. In FIG. 2A, centering mechanism 220 and stent 202 are shown in their expanded configurations in which centering ring 222 has an expanded diameter that is greater than an expanded diameter of tubular stent 202 such that centering ring 222 is radially spaced apart from the outer surface of tubular stent 202 with spokes 224 radially extending between tubular stent 202 and centering ring 222. When expanded, spokes 224 are substantially straight or linear and centering mechanism 220 has a flat profile that extends transverse with respect to the longitudinal axis of transcatheter valve prosthesis 200. Depending upon the size of the patient, the expanded diameter of centering ring 222 may vary between 20 mm and 40 mm. Centering ring 222 is required to be sized greater than the opening defined by the native valve annulus so that the centering ring contacts or abuts against an abutment surface defined by the native valve annulus during use thereof. Since centering mechanism 220 is coupled to the outer surface of valve prosthesis 200, longitudinal placement and/or the size and shape thereof may be adjusted or adapted according to each application and to a patient's unique needs. For example, depending on the anatomy of the particular patient, centering mechanism 220 may be placed closer to second end 218 than shown and/or centering ring 222 may have an expanded diameter that is greater or less than the expanded diameter shown in FIG. 2.

FIG. 3A is a cross-sectional view taken along line A-A of FIG. 2, with leaflets 204 removed for sake of illustration only, with centering mechanism 220 and stent 202 shown in their compressed or delivery configurations. In the compressed or delivery configuration, spokes 224 bend or radially collapse such that the diameter of ring 222 is approximately equal to or slightly larger than the compressed or delivery diameter of stent 202. Centering ring 222 and spokes 224 are formed from a self-expanding material and shape-set in the deployed or expanded configuration such that centering mechanism 220 returns to the expanded or deployed configuration of FIGS. 2 and 2A after being radially compressed or constricted for delivery.

Although centering mechanism 220 is shown with eight spokes 224 circumferentially spaced apart with respect to tubular stent 202, centering mechanism 220 may include a greater number of spokes or a fewer number of spokes, depending upon application. Each spoke 224 is an individual or separate strand of material having opposing ends thereof attached or fixed to ring 222 and tubular stent 202. The opposing ends of each spoke 224 may be attached to ring 222 and tubular stent 202 by any suitable means known to those skilled in the art, for example and not by way of limitation, welding, adhesive, suture, or mechanical coupling. In an embodiment hereof, centering mechanism 220 is also configured to circumferentially center valve prosthesis 200 within the native valve annulus. More particularly, an outer surface of centering mechanism 220 is sized and configured to contact and abut against an inner surface of the native valve annulus and spokes 224 are configured to have sufficient rigidity to circumferentially center valve prosthesis 220. In an embodiment hereof, spokes 224 may have a thickness between 0.05 mm and 0.5 mm in order to be achieve the desired circumferentially centering objective while still being flexible enough to collapse for delivery.

Figure 4:
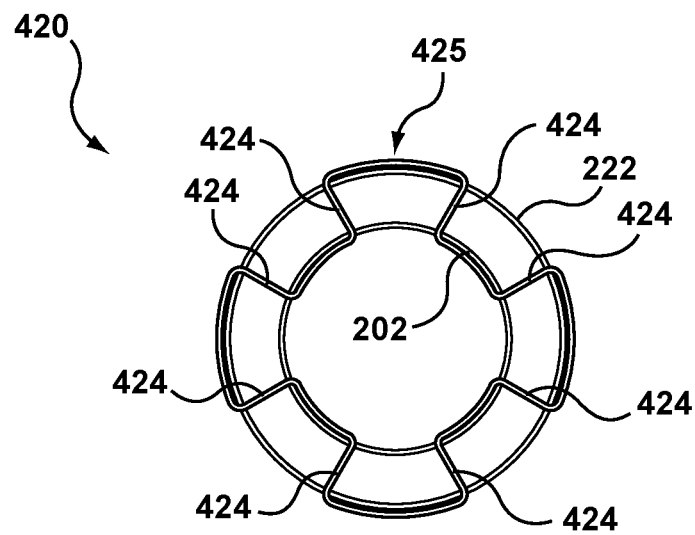
FIG. 4 is a cross-sectional view of a transcatheter valve prosthesis having an integral centering mechanism according to another embodiment hereof, wherein a strand in woven between a stent and a centering ring to form a plurality of spokes, the valve prosthesis and the centering mechanism being shown in their expanded or deployed configurations.

In another embodiment hereof, the plurality of spokes may be formed with a single strand of material that is woven between the tubular stent and the centering ring. More particularly, as shown on FIG. 4, spokes 424 are formed via a single strand 425 of material. Strand 425 is woven between stent 202 and centering ring 222 in order to form a plurality of spokes 424 radially extending between tubular stent 202 and centering ring 222. Strand 425 may be woven between the openings or cells formed within stent 202 and looped around the centering ring 222. After the desired number of circumferentially spaced apart spokes 424 are formed, the ends of strand 425 may be coupled together such that strand 425 is a ring formed from a self-expanding material and shape-set in the deployed or expanded configuration such that centering mechanism 420 returns to the expanded or deployed configuration of FIG. 4 after being radially compressed or constricted for delivery.

Figure 5:
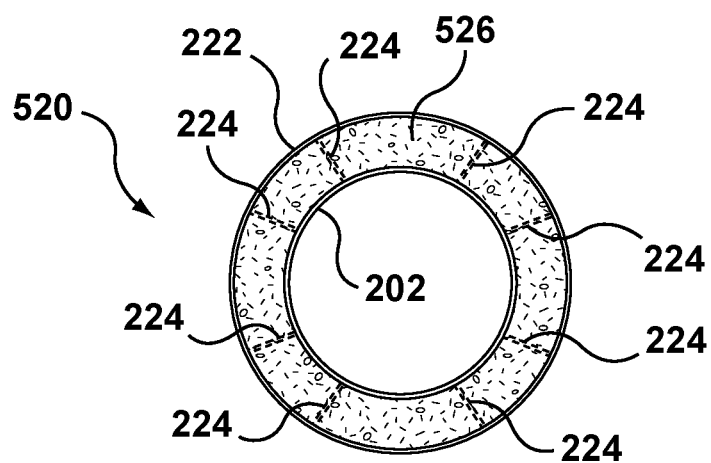
FIG. 5 is a cross-sectional view of a transcatheter valve prosthesis having an integral centering mechanism according to another embodiment hereof, wherein the valve prosthesis includes a flexible skirt, the valve prosthesis and the centering mechanism being shown in their expanded or deployed configurations.

In another embodiment hereof, a flexible skirt material may be attached to an outer surface of the centering mechanism. More particularly, as shown in the embodiment of FIG. 5, a centering mechanism 520 is similar to centering mechanism 420 and includes self-expanding centering ring 222 and a plurality of spokes 224 radially extending between tubular stent 202 and centering ring 222. In addition, a flexible skirt 526 is disposed over an outer surface of centering ring 222 and spokes 224. The skirt is formed from a low-porosity woven fabric or pericardial tissue and serves as a sealing element in situ to block or prevent retrograde blood flow around the outside of tubular stent 202, thereby minimizing and/or eliminating any paravalvular leakage at the implantation site.

Delivery and deployment of transcatheter valve prosthesis 200 will now be described with reference to FIGS. 6-9. A valve delivery system 630 having transcatheter valve prosthesis 200 mounted thereon is percutaneously introduced into the vasculature, with transcatheter valve prosthesis 200 in a delivery configuration. Valve delivery system 630 includes a tubular outer shaft 632 defining a lumen therethrough and a tubular inner shaft 636 (shown on FIG. 7) defining a lumen there-through. A distal tip 634 is coupled to a distal end of inner shaft 636. Inner shaft 636 is concentrically disposed within the lumen of outer shaft 632, and the lumen of inner shaft 636 may be sized to slidingly receive a guidewire (not shown) such that valve delivery system 630 may be tracked over the guidewire during delivery of transcatheter valve prosthesis 200. In the delivery configuration of FIG. 1, a distal portion of outer shaft 632 is disposed over transcatheter valve prosthesis 200 to compressively retain the transcatheter valve prosthesis in crimped engagement with inner shaft 636. Valve delivery system 630 may be one of, but is not limited to, the delivery systems described in U.S. Patent Publication No. 2011/0245917 to Savage et al., U.S. Patent Publication No. 2011/0251675 to Dwork, U.S. Patent Publication No. 2011/0251681 to Shipley et al., U.S. Patent Publication No. 2011/0251682 to Murray, III et al., and U.S. Patent Publication No. 2011/0264202 to Murray, III et al., each of which is herein incorporated by reference in its entirety.

Figure 6:
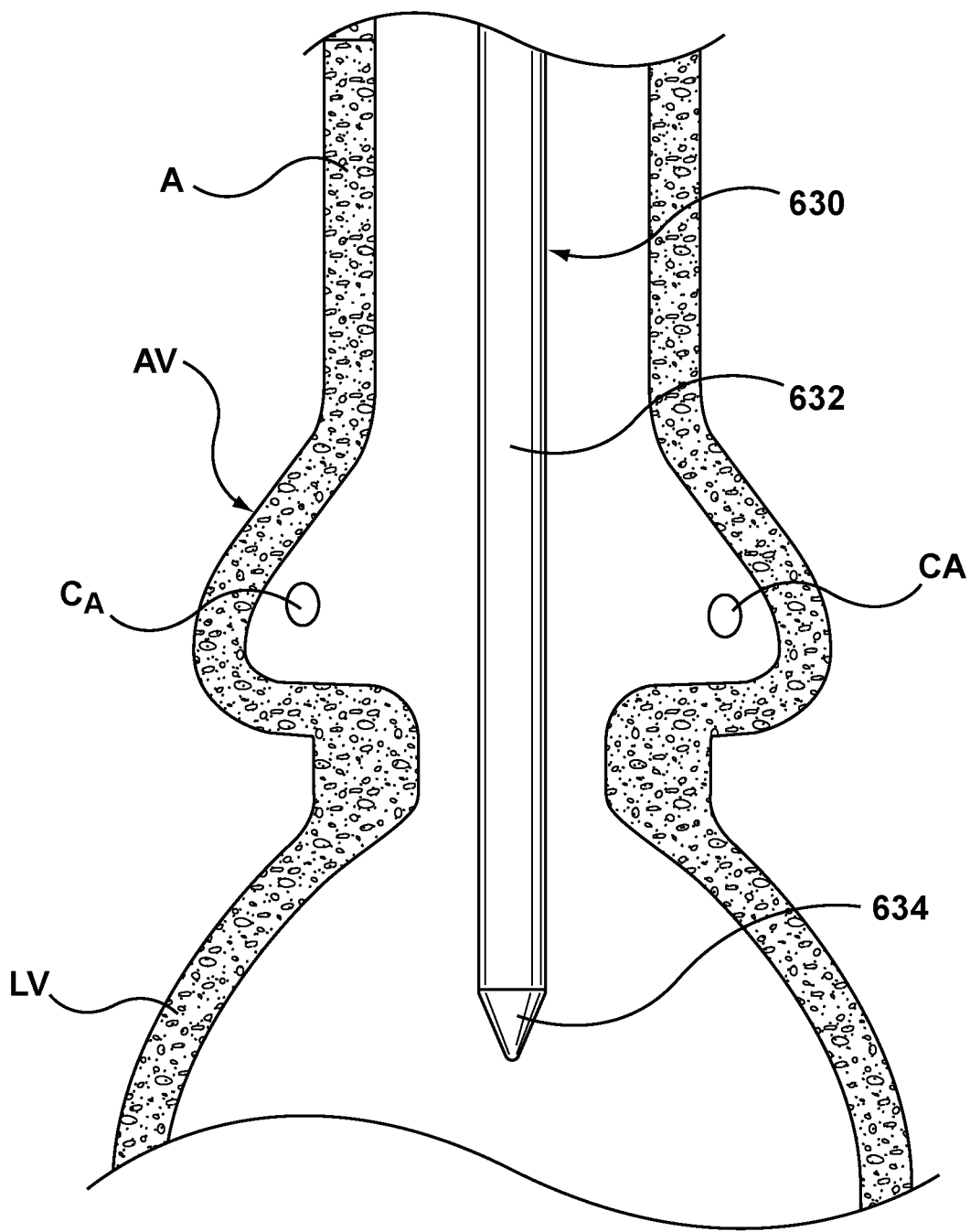
FIG. 6 is an illustration of the transcatheter valve prosthesis of FIG. 2 being delivered to a native aortic valve, wherein the valve prosthesis and the centering mechanism are compressed within a delivery system.

Valve delivery system 630 is tracked through the vasculature until transcatheter valve prosthesis 200 is positioned within the native valve annulus as shown in FIG. 6. During delivery, transcatheter valve prosthesis 200 remains compressed within valve delivery system 630. Delivery of transcatheter valve prosthesis 200 may be accomplished in accordance with techniques known in the field of interventional cardiology and/or interventional radiology. In an embodiment hereof, transcatheter valve prosthesis 200 is configured for implantation in a target diseased native aortic valve AV that extends between a patient's left ventricle LV and a patient's aorta A. The coronary arteries $C_A$ are also shown on the sectional view of FIG. 6. Transcatheter valve prosthesis 200 is configured for implantation via a percutaneous transfemoral approach and valve delivery system 630 is transluminally advanced in a retrograde approach through the vasculature to the treatment site. More particularly, valve delivery system 630 is tracked through the femoral artery, up the aorta and around the aortic arch in order to access the native aortic valve AV. Transcatheter valve prosthesis 200 may also be positioned within the desired area of the heart via different delivery methods known in the art for accessing heart valves.

Figure 7:
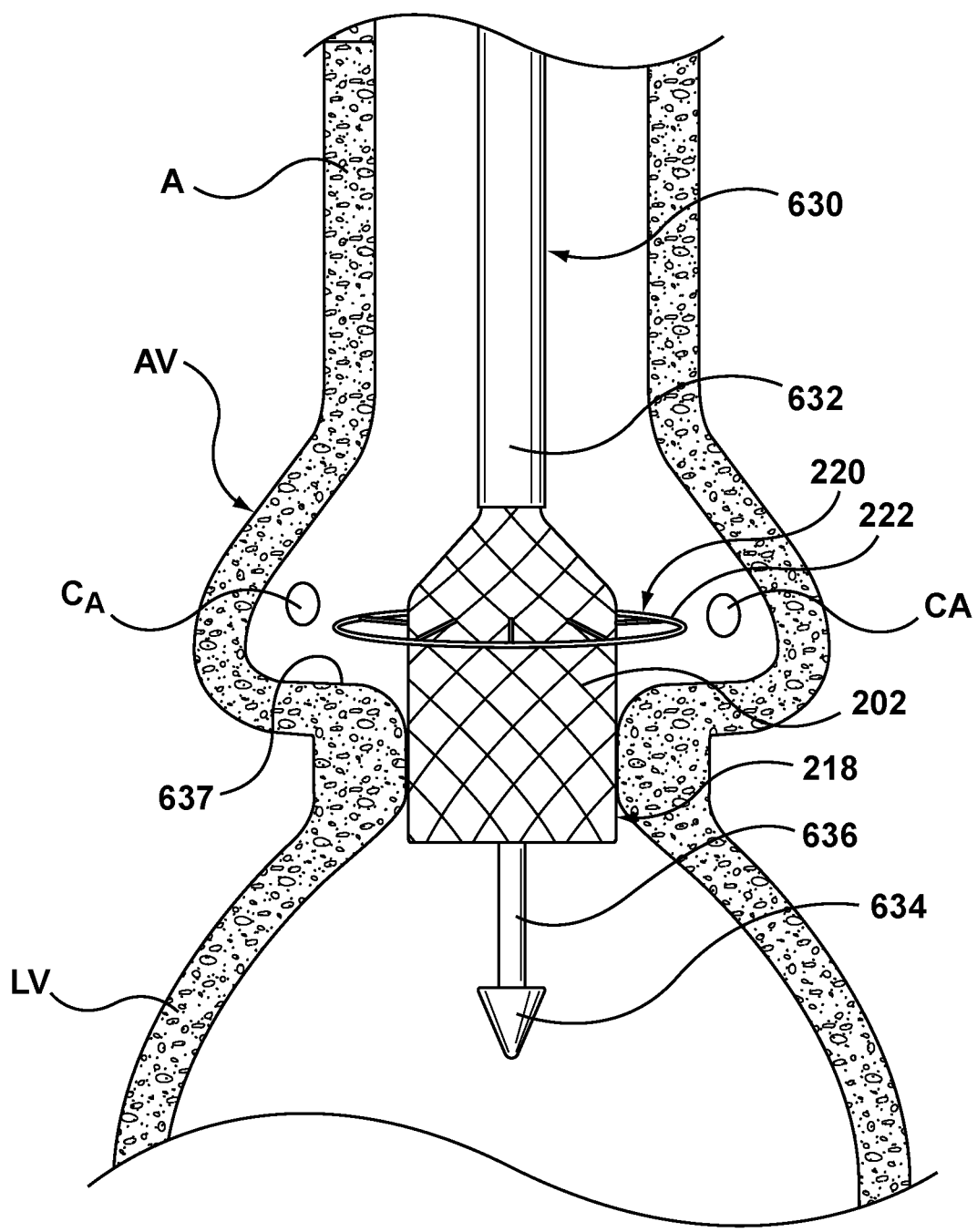
FIG. 7 is an illustration of the transcatheter valve prosthesis of FIG. 2 being deployed within a native aortic valve, wherein an inflow end of the valve prosthesis and the centering mechanism are deployed.

After transcatheter valve prosthesis 200 is positioned within the native valve annulus as desired, at least second or inflow end 218 of tubular stent 202 and centering mechanism 220 are deployed into an expanded configuration as shown in FIG. 7. More particularly, outer shaft 632 is retracted to release second or inflow end 218 of tubular stent 202 and centering mechanism 220, which are permitted to resume their shape-set, deployed configurations via self-expansion. At this stage of deployment, centering ring 222 is positioned in situ slightly above an abutment surface 637 defined by the native valve annulus.

Figure 8:
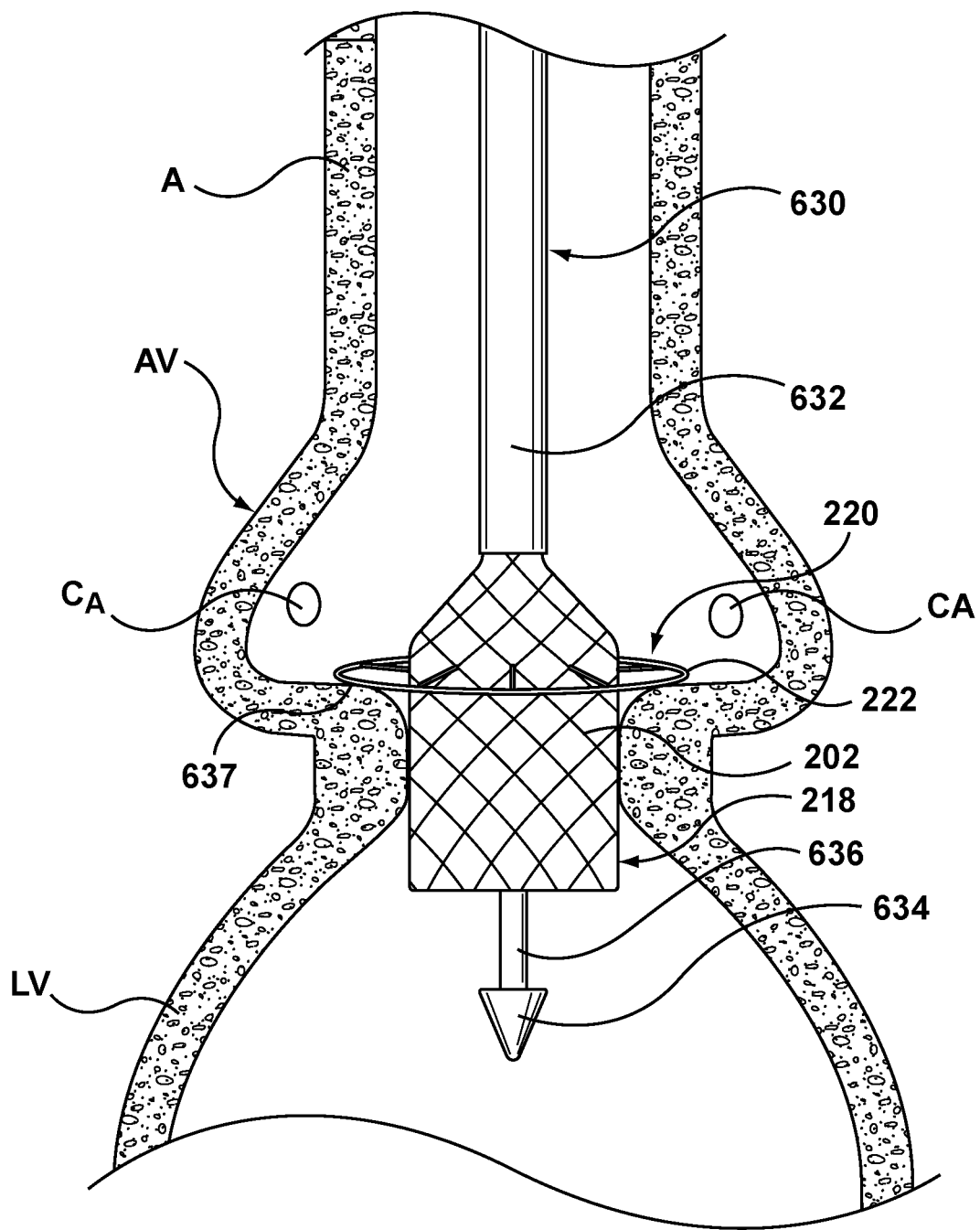
FIG. 8 is an illustration of the transcatheter valve prosthesis of FIG. 2 being deployed within a native aortic valve, wherein the centering mechanism is positioned against the native aortic valve.

Valve delivery system 630 is then manipulated in order to catch or contact deployed centering mechanism 220 onto abutment surface 637 of the native valve annulus. More particularly, valve delivery system 630 is distally advanced in order to translate or move valve prosthesis 200 and centering mechanism 220 until centering ring 222 contacts or abuts against abutment surface 637 of the native valve annulus as shown in FIG. 8. As such, centering ring 222 is utilized as a depth marker or reference point to longitudinally center valve prosthesis 200 by preventing the valve prosthesis from being positioned too deep or too shallow within the left ventricle LV.

Figure 9:
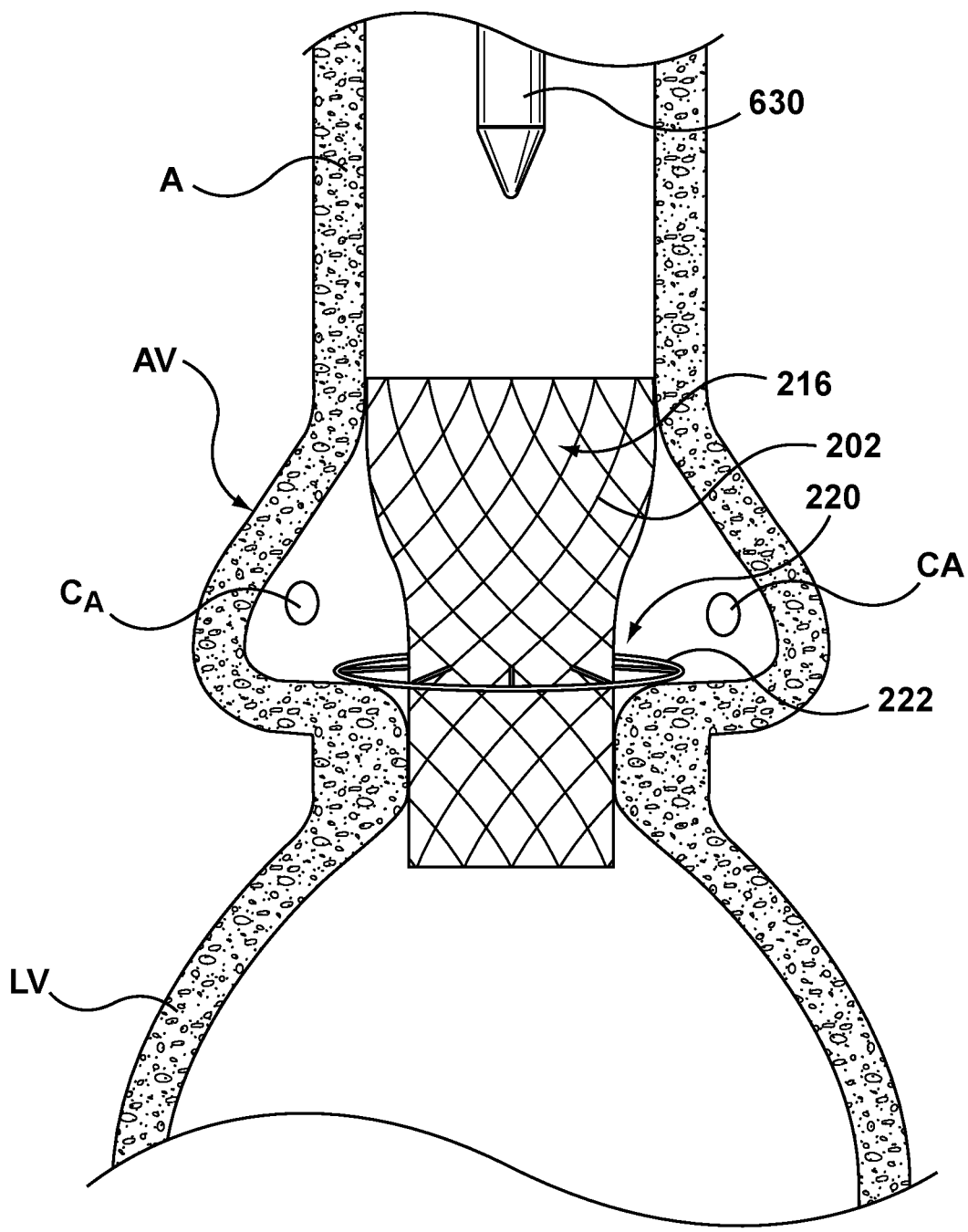
FIG. 9 is an illustration of the transcatheter valve prosthesis of FIG. 2 being deployed within a native aortic valve, wherein an outflow end of the valve prosthesis is deployed.

Once centering ring 222 is positioned as desired, the first or outflow end 216 of tubular stent 202 is deployed into the expanded configuration as shown in FIG. 9. More particularly, outer shaft 632 is retracted to release first or outflow end 216 of tubular stent 202, which is permitted to resume its shape-set, deployed configuration via self-expansion. If the position of transcatheter valve prosthesis 200 needs to be adjusted after deployment, transcatheter valve prosthesis 200 including integral centering mechanism 220 may be recaptured by distally advancing outer shaft 632 there-over to return transcatheter valve prosthesis 200 and integral centering mechanism 220 to their delivery configurations. When transcatheter valve prosthesis 200 is positioned as desired, valve delivery catheter 630 is then removed and transcatheter valve prosthesis 200 remains deployed within the native target heart valve.

Figure 10:
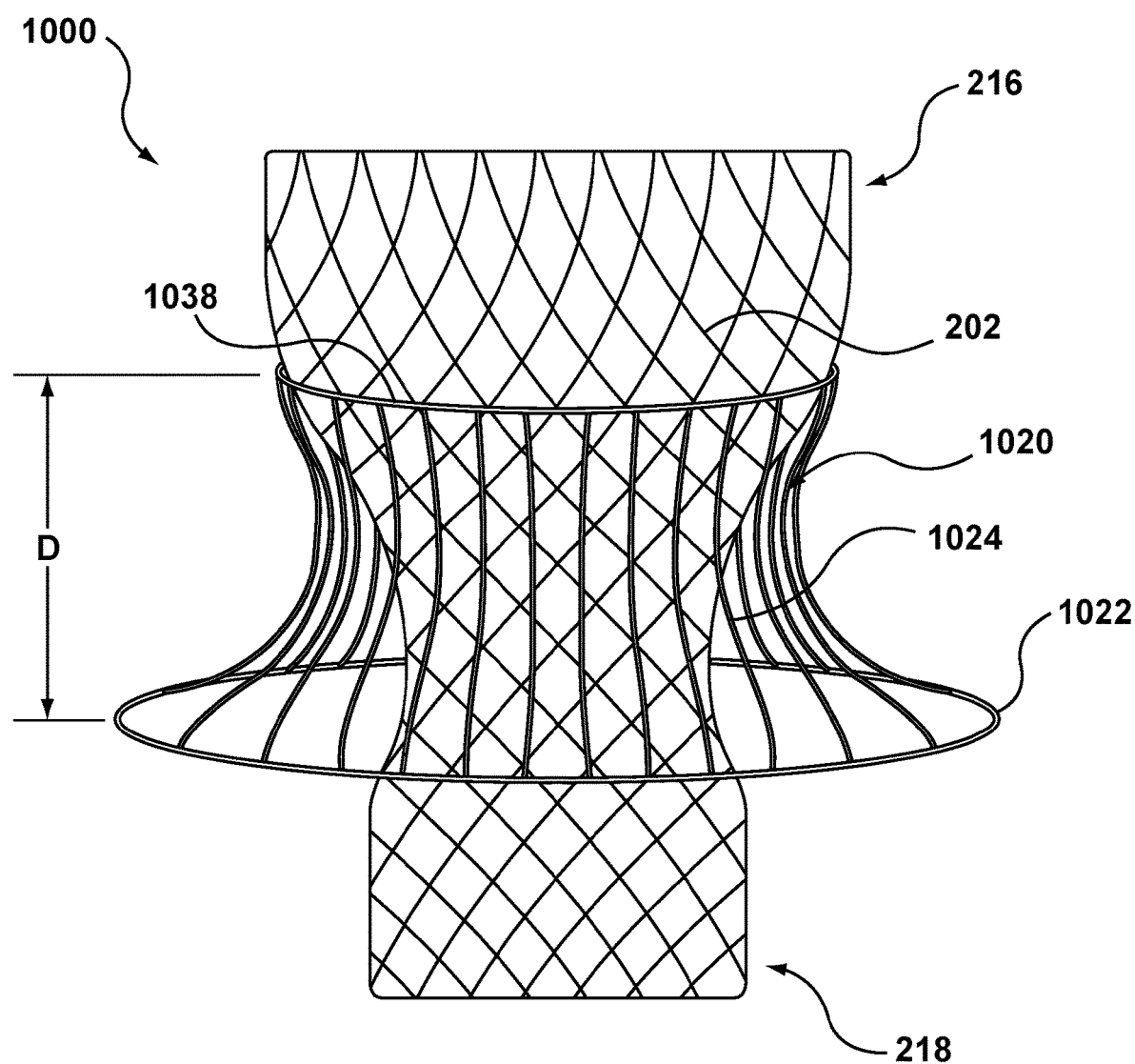
FIG. 10 is a side view illustration of a transcatheter valve prosthesis having an integral centering mechanism according to another embodiment hereof, wherein the valve prosthesis and the centering mechanism are in expanded or deployed configurations.
Figure 11:
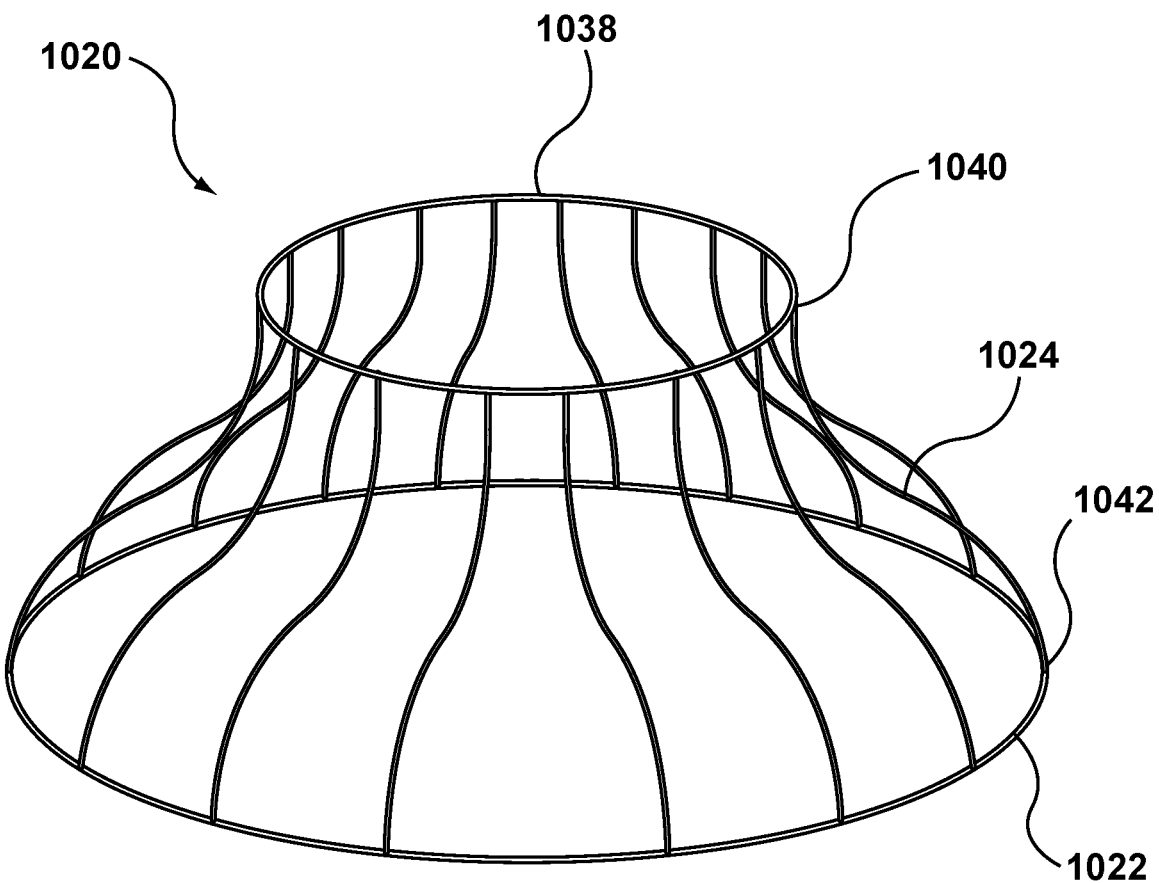
FIG. 11 is a perspective view of the centering mechanism of FIG. 10 removed from the other components of the valve prosthesis for illustrative purposes only, wherein the centering mechanism is in its expanded or deployed configuration.

In the embodiments of FIGS. 2-9, centering mechanism 220 has a flat profile that extends transverse with respect to the longitudinal axis of transcatheter valve prosthesis 200. A centering mechanism 1020 having a different configuration or profile is shown in FIGS. 10 and 11. FIG. 10 is a side view of centering mechanism 1020 coupled to and encircling an outer surface of tubular stent 202, while FIG. 11 is a perspective view of centering mechanism 1020 removed from the tubular stent for illustrative purposes only. Centering mechanism 1020 and stent 202 are shown in their expanded configurations in FIGS. 10 and 11. Similar to centering mechanism 220, centering mechanism 1020 includes a self-expanding centering ring 1022 and a plurality of spokes 1024 radially extending between tubular stent 202 and centering ring 1022. In their expanded configurations, centering ring 1022 has an expanded diameter that is greater than an expanded diameter of tubular stent 202 such that centering ring 1022 is radially spaced apart from the outer surface of tubular stent 202. However, in this embodiment, centering mechanism 1020 also includes a base ring 1038 attached to tubular stent 202 which has expanded diameter equal to the expanded diameter of the tubular stent. Base ring 1038 and centering ring 1022 are longitudinally spaced apart by a distance D, with base ring 1038 being positioned proximal to centering ring 1022. In an embodiment, distance D may vary between 0.25 inches and 2.00 inches. Base ring 1038 may be attached to stent 202 by any suitable means known to those skilled in the art, for example and not by way of limitation, welding, adhesive, suture, or mechanical coupling.

Figure 12:
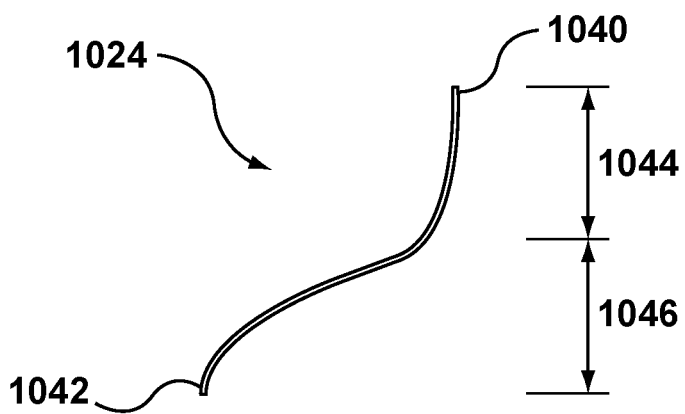
FIG. 12 is a side view of a single spoke of the centering mechanism of FIG. 11, wherein the spoke is in its expanded or deployed configuration.

Centering mechanism 1020 may include a greater number of spokes or a fewer number of spokes, depending upon application. Each spoke 1024 is an individual or separate strand of material having opposing ends 1040, 1042 attached or fixed to base ring 1038 and centering ring 1022, respectively. A side view of a single spoke 1024 is shown in FIG. 12, the spoke being removed from the centering mechanism for illustration purposes only. Spokes 1024, as well as base ring 1038 and centering ring 1022, are formed from a self-expanding material and shape-set in the deployed or expanded configuration such that centering mechanism 1020 returns to the expanded or deployed configuration of FIGS. 10 and 11 after being radially compressed or constricted for delivery. In its deployed or expanded configuration, each spoke 1024 may be considered to include a first longitudinal portion 1044 and a second longitudinal portion 1046. First and second longitudinal portions 1044, 1046 are continuous or integral with each other but are described separately herein due to their differing shapes. In an embodiment, first and second longitudinal portions 1044, 1046 each extend one-half of the total length of spoke 1024. First longitudinal portion 1044 is substantially straight or linear, while second longitudinal portion 1046 curves or flares radially outward. The shapes of first and second longitudinal portions 1044, 1046 match or correspond with the shape of a native aortic valve.

When deployed, as will be described in more detail with respect to FIGS. 14-15, centering ring 1022 is configured to abut against a native valve annulus to both circumferentially and longitudinally center valve prosthesis 1000 within the native valve annulus. As described with respect to centering ring 222, centering ring 1022 is configured to abut against an abutment surface of a native valve annulus such that centering ring 222 serves as a depth marker or reference point to longitudinally center valve prosthesis 1000 by preventing the valve prosthesis from being positioned too deep or too shallow within the left ventricle. In addition, an outer surface of centering mechanism 1020 is sized and configured to contact and abut against an inner surface of the native valve annulus and spokes 1024 are configured to have sufficient rigidity to circumferentially center valve prosthesis 1000. Depending upon the size of the patient, the expanded diameter of centering ring 1022 may vary between 0.50 inches and 3.00 inches. In an embodiment hereof, spokes 1024 may have a thickness between 0.01 inches and 0.2 inches in order to be achieve the desired circumferentially centering objective while still being flexible enough to collapse for delivery.

Delivery and deployment of transcatheter valve prosthesis 1000 will now be described with reference to FIGS. 13-15. Valve delivery system 630 having transcatheter valve prosthesis 1000 mounted thereon is percutaneously introduced into the vasculature, with transcatheter valve prosthesis 1000 in a delivery configuration. As described with respect to FIG. 6, valve delivery system 630 includes tubular outer shaft 632 tubular inner shaft 636, and a distal tip 634 which is coupled to a distal end of the inner shaft. In the delivery configuration of FIG. 13, a distal portion of outer shaft 632 is disposed over transcatheter valve prosthesis 1000 to compressively retain the transcatheter valve prosthesis in crimped engagement with inner shaft 636. FIG. 13A is a side view of centering mechanism 1020 and stent 1002 shown in their compressed or delivery configurations, although the delivery system is not shown for sake of clarity. In the compressed or delivery configuration, base ring 1038 and centering ring 1022 each have a compressed diameter that is substantially equal to or only slightly greater than a compressed or delivery diameter of tubular stent 202. Spokes 1024 are substantially straight or linear, and lie flat or flush with an outer surface of compressed tubular stent 202. Since centering ring 1022 is not coupled or attached to the outer surface of tubular stent 202, centering ring 1022 slides or moves along the outer surface of tubular stent 202 towards second or inflow end 218 of tubular stent 202 in order to allow spokes 1024 to straighten into their delivery configurations.

Figure 13:
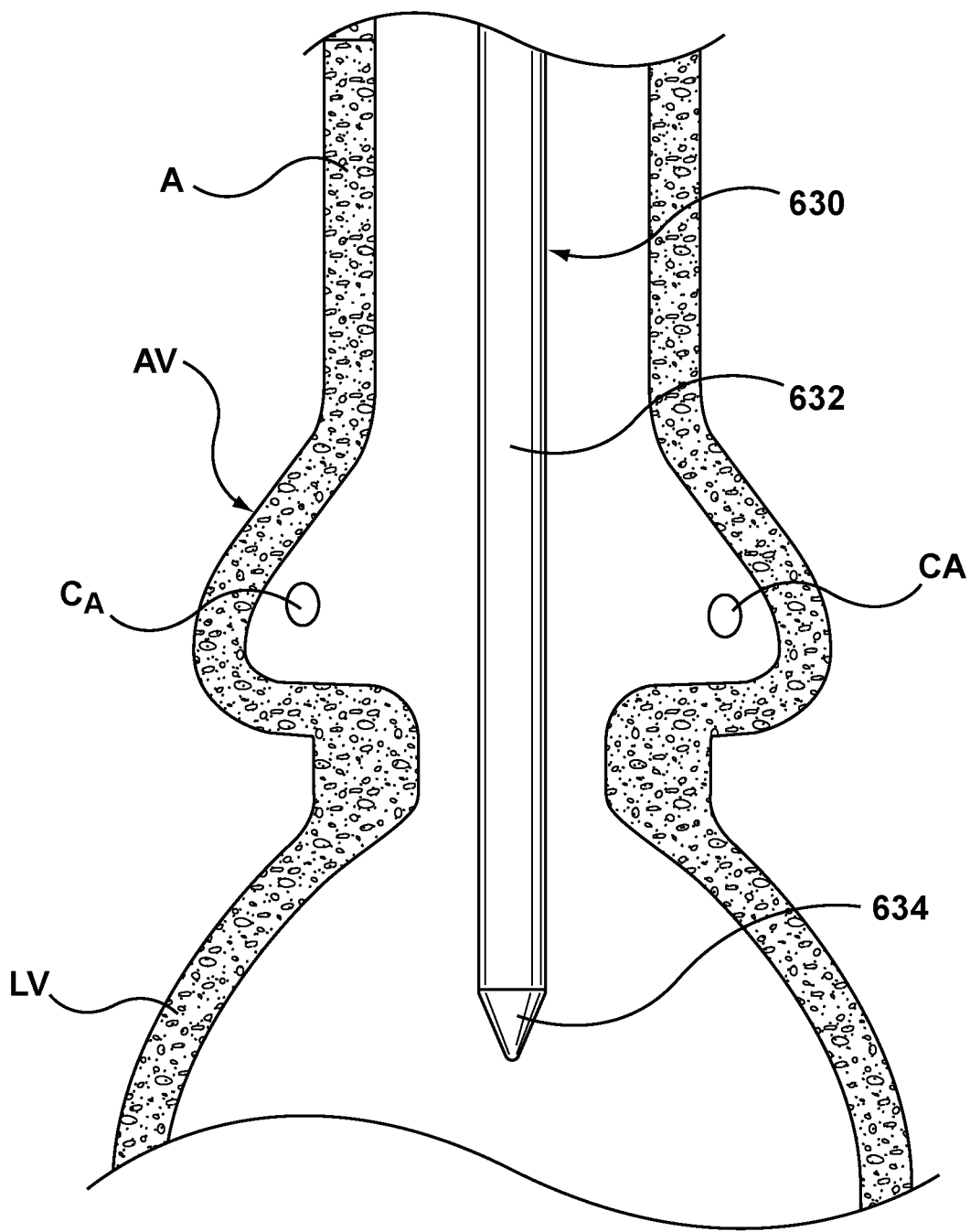
FIG. 13 is an illustration of the transcatheter valve prosthesis of FIG. 10 being delivered to a native aortic valve, wherein the valve prosthesis and the centering mechanism are compressed within a delivery system.
Figure 13A:
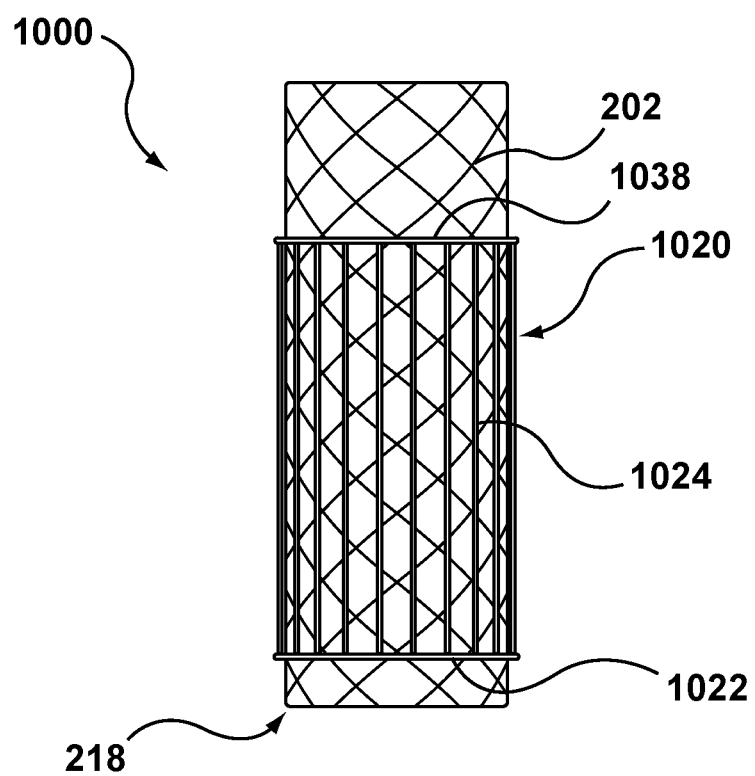
FIG. 13A is a side view of the transcatheter valve prosthesis of FIG. 10, wherein the valve prosthesis and the centering mechanism are in compressed or delivery configurations.

Valve delivery system 630 is tracked through the vasculature until transcatheter valve prosthesis 1000 is positioned within the native valve annulus as shown in FIG. 13. During delivery, transcatheter valve prosthesis 1000 remains compressed within valve delivery system 630. Delivery of transcatheter valve prosthesis 1000 may be accomplished in accordance with techniques known in the field of interventional cardiology and/or interventional radiology. In an embodiment hereof, transcatheter valve prosthesis 1000 is configured for implantation in a target diseased native aortic valve AV that extends between a patient's left ventricle LV and a patient's aorta A. The coronary arteries $C_A$ are also shown on the sectional view of FIG. 13. Transcatheter valve prosthesis 1000 is configured for implantation via a percutaneous transfemoral approach and valve delivery system 630 is transluminally advanced in a retrograde approach through the vasculature to the treatment site. More particularly, valve delivery system 630 is tracked through the femoral artery, up the aorta and around the aortic arch in order to access the native aortic valve AV. Transcatheter valve prosthesis 1000 may also be positioned within the desired area of the heart via different delivery methods known in the art for accessing heart valves.

Figure 14:
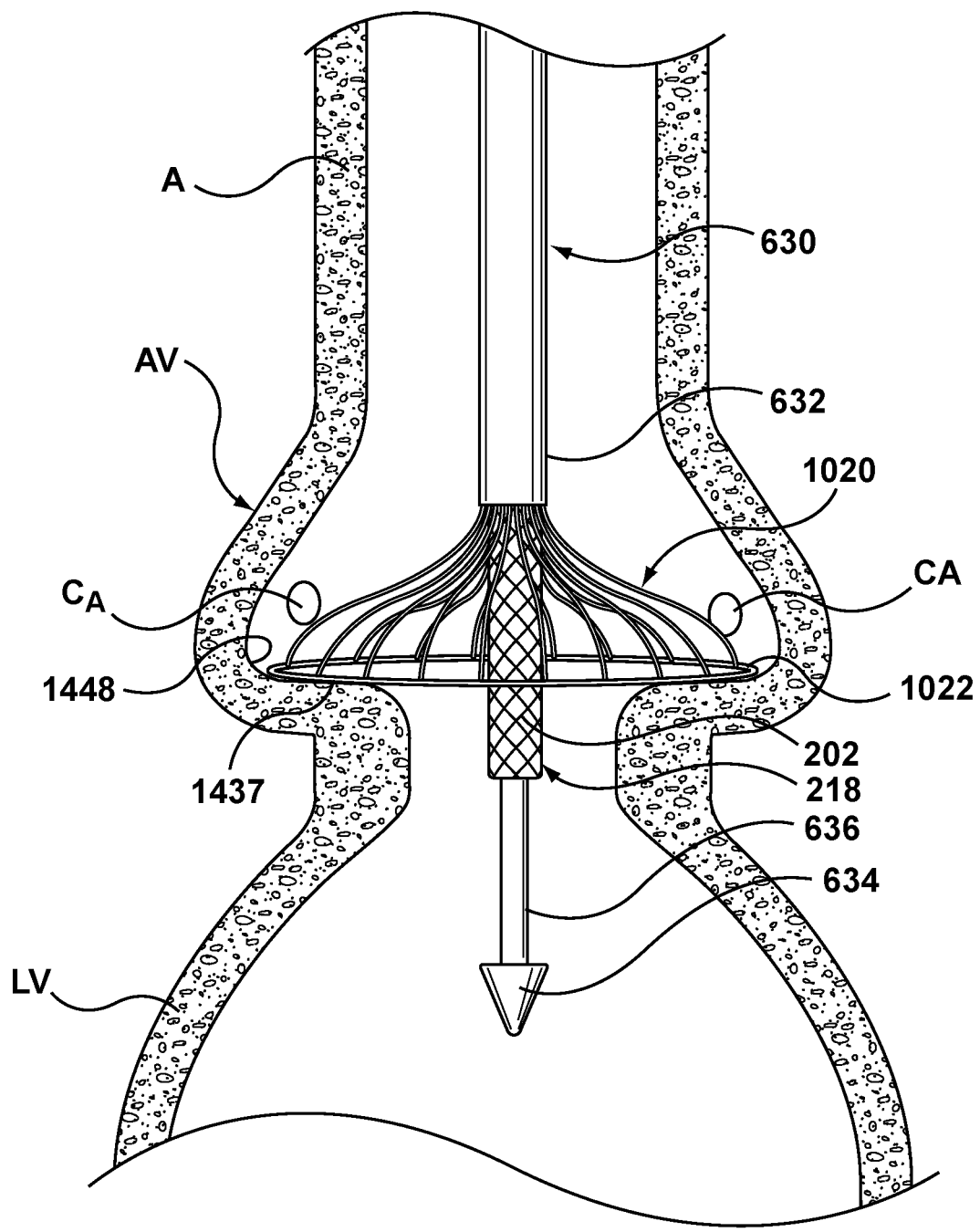
FIG. 14 is an illustration of the transcatheter valve prosthesis of FIG. 10 being deployed within a native aortic valve, wherein the centering mechanism is deployed and the inflow end of the valve prosthesis is partially deployed.
Figure 15:
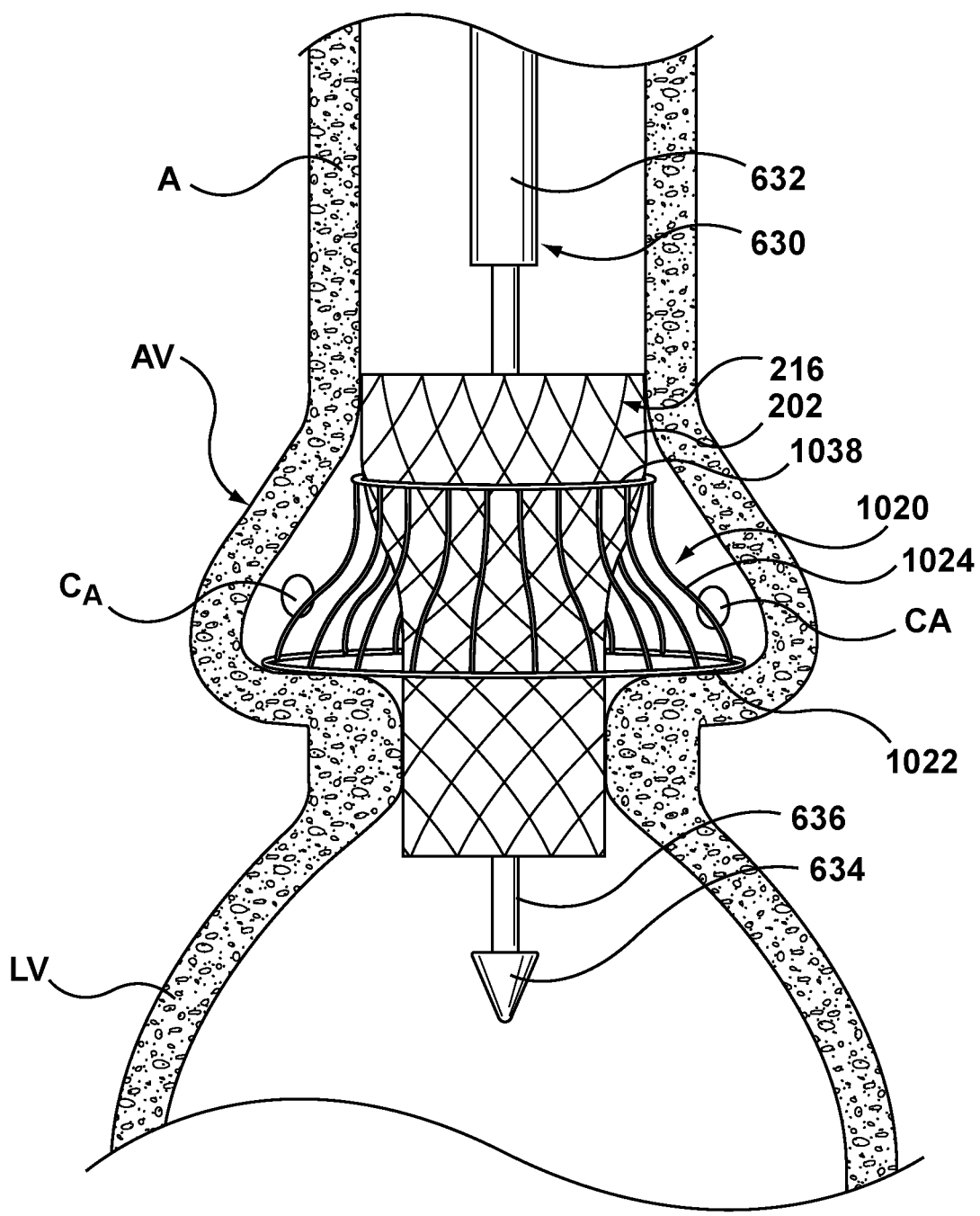
FIG. 15 is an illustration of the transcatheter valve prosthesis of FIG. 10 deployed within a native aortic valve, wherein the centering mechanism and the valve prosthesis are fully deployed.

After transcatheter valve prosthesis 1000 is positioned within the native valve annulus as desired, at least second or inflow end 218 of tubular stent 202 and centering mechanism 1020 are deployed into an expanded configuration as shown in FIG. 14. More particularly, outer shaft 632 is retracted to release second or inflow end 218 of tubular stent 202 and centering mechanism 1020, which are permitted to resume their shape-set, deployed configurations via self-expansion. However, due to the geometry/profile and radial force of centering mechanism 1020, centering mechanism 1020 is configured to self-expand at a faster rate than tubular stent 202 as shown in FIG. 14. As such, centering mechanism 1020 reaches its deployed or expanded configuration while tubular stent 202 is still in a compressed configuration or is only partially deployed in that second or inflow end 218 of tubular stent 202 has not yet reached its fully deployed or expanded diameter.

In FIG. 14, centering ring 1022 is shown deployed onto abutment surface 1437 of the native valve annulus. As such, centering ring 1022 is utilized as a depth marker or reference point to longitudinally center valve prosthesis 1000 by preventing the valve prosthesis from being positioned too deep or too shallow within the left ventricle LV. However, if centering ring 1022 deploys above abutment surface 1437 of the native valve annulus, valve delivery system 630 may be manipulated in order to catch or contact deployed centering mechanism 1020 onto abutment surface 1437 of the native valve annulus. More particularly, valve delivery system 630 may be distally advanced in order to translate or move valve prosthesis 1000 and centering mechanism 1020 until centering ring 1022 contacts or abuts against abutment surface 1437 of the native valve annulus as shown in FIG. 14.

When fully deployed, centering ring 1022 contacts or abuts against an inner surface 1448 of the native valve annulus as shown in FIG. 14 and thereby circumferentially self-centers itself within the native valve annulus. As such, since centering ring 1022 is circumferentially centered, centering mechanism 1020 pulls or locates tubular stent 202 into a circumferentially centered positioned as the tubular stent 202 expands to its fully deployed configuration as shown in FIG. 15. If not previously released from the delivery system, first or outflow end 216 of tubular stent 202 is then deployed into the expanded configuration via retraction of outer shaft 632 as shown in FIG. 15. If the position of transcatheter valve prosthesis 1000 needs to be adjusted after deployment, transcatheter valve prosthesis 1000 including integral centering mechanism 1020 may be recaptured by distally advancing outer shaft 632 there-over to return transcatheter valve prosthesis 1000 and integral centering mechanism 1020 to their delivery configurations. When transcatheter valve prosthesis 1000 is positioned as desired, valve delivery catheter 630 is then removed and transcatheter valve prosthesis 1000 remains deployed within the native target heart valve. Deployment of transcatheter valve prosthesis 1000 may thus be considered to occur via two consecutive stages with a first stage of deployment including deployment of centering mechanism 1020 and a second stage of deployment including deployment of tubular stent 202 having a prosthetic valve component therein.

In an embodiment hereof, a flexible skirt material may be attached to an outer surface of centering mechanism 1020.

Figure 16:
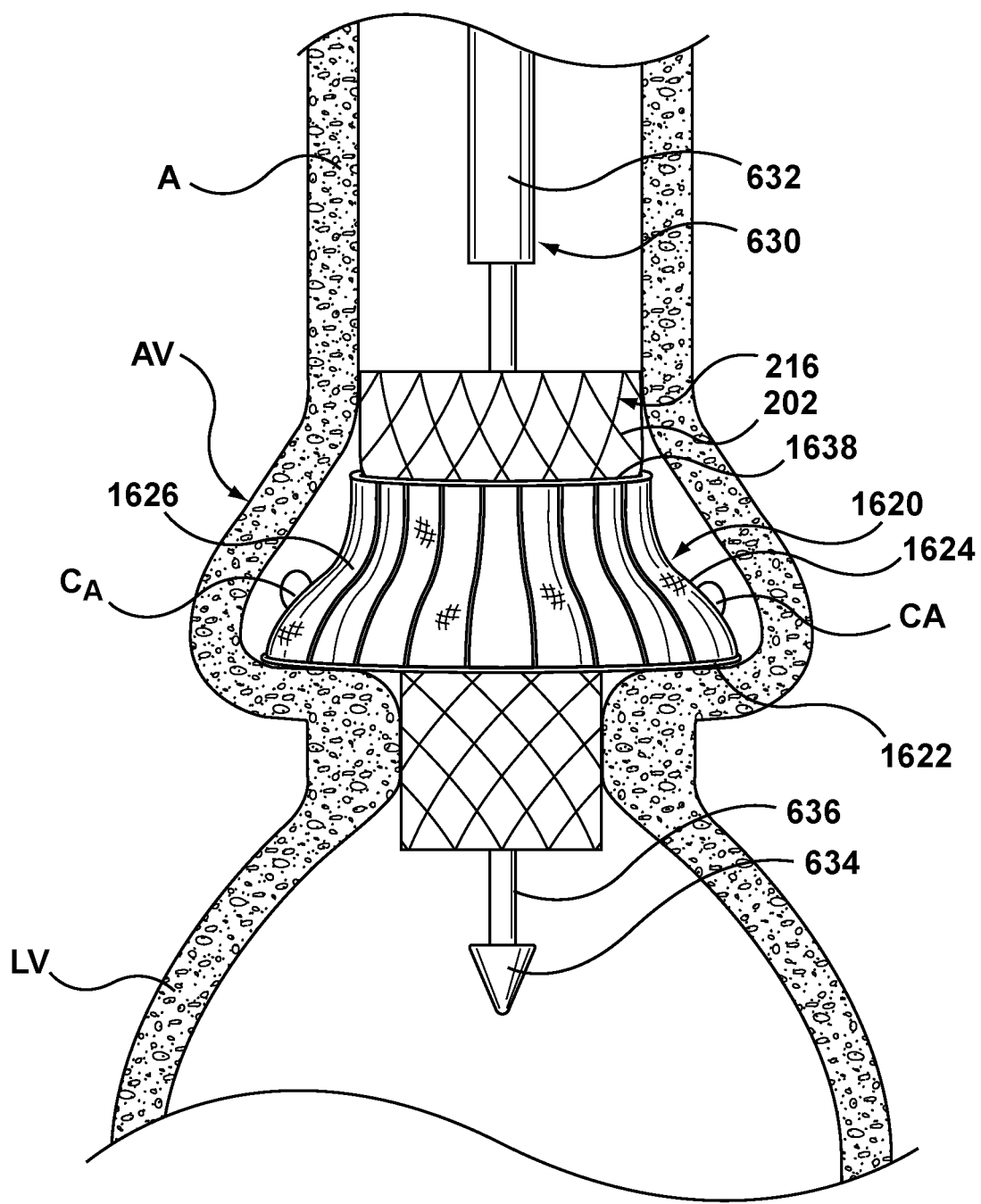
FIG. 16 is an illustration of a transcatheter valve prosthesis according to another embodiment hereof deployed within a native aortic valve, wherein the transcatheter valve prosthesis includes a flexible skirt.

More particularly, as shown in the embodiment of FIG. 16, a centering mechanism 1620 is similar to centering mechanism 1020 and includes self-expanding centering ring 1622, a base ring 1638, and a plurality of spokes 1624 radially extending between tubular stent 202 and centering ring 1622. In addition, a flexible skirt 1626 is disposed over an outer surface of centering ring 1622 and spokes 1624. The skirt is formed from a low-porosity woven fabric or pericardial tissue and serves as a sealing element in situ to block or prevent retrograde blood flow around the outside of tubular stent 202, thereby minimizing and/or eliminating any paravalvular leakage at the implantation site. Since skirt 1626 is attached to self-expanding centering ring 1622, centering ring 1622 operates to radially extend or deploy an edge of skirt 1626 outwardly away from stent 202 to form an open-ended annular pocket or compartment 1649 between an inner surface of the skirt and the outer surface of the tubular stent. Open-ended pocket 1649 catches blood flow around the outer perimeter of the prosthesis and blocks any retrograde flow within the native valve, thereby preventing undesired regurgitation and preventing blood stagnation in and around the native valve sinuses. Open-ended pocket 1649 functions as a continuous circumferential seal around transcatheter valve prosthesis 1600 to block or prevent blood flow around the outer perimeter of the prosthesis, thereby minimizing and/or eliminating any paravalvular leakage at the implantation site.

Figure 17:
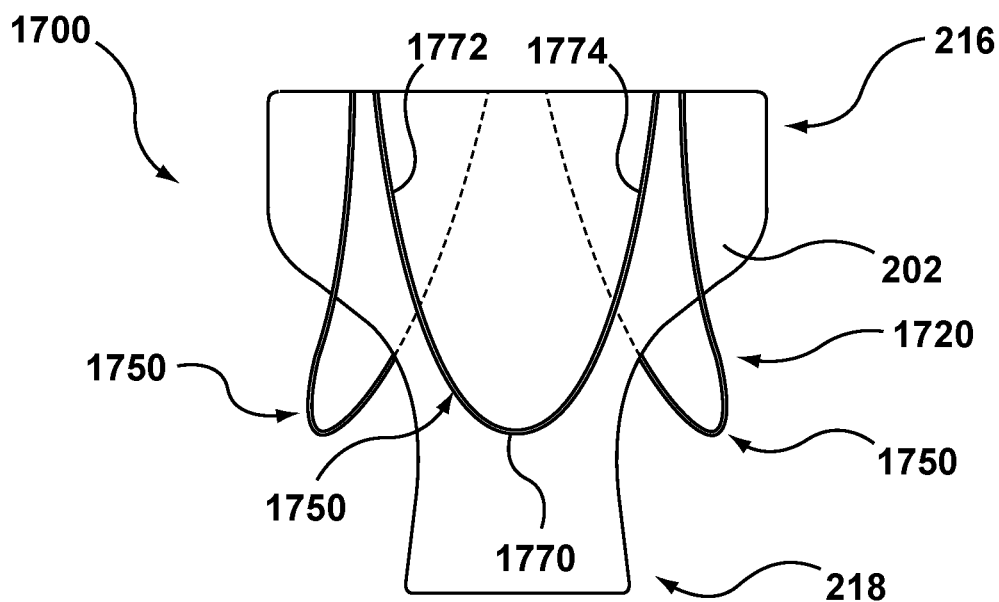
FIG. 17 is a side view illustration of a transcatheter valve prosthesis having an integral centering mechanism according to another embodiment hereof, the centering mechanism including a plurality of loops, wherein the valve prosthesis and the centering mechanism are in expanded or deployed configurations.

A centering mechanism 1720 including a plurality of self-expanding loops is shown in FIG. 17. Centering mechanism 1720 and stent 202 are shown in their expanded configurations in FIG. 17 and in their delivery configurations in FIG. 18, although only the outline or profile of stent 202 is shown and the wireframe pattern is omitted for sake of clarity. In this embodiment, centering mechanism 1720 includes a plurality of self-expanding loops 1750 that may be deployed within the cusps of the aortic annulus to longitudinally center transcatheter valve prosthesis 1700 within the native valve annulus. The three self-expanding loops 1750 are circumferentially spaced apart at approximately 120 degree intervals around first or outflow end 216 of tubular stent 202. Although centering mechanism 1720 is shown with three self-expanding loops 1750, centering mechanism 1720 may include a greater number of self-expanding loops or a fewer number of self-expanding loops, depending upon application.

Loops 1750 are generally shown in the figures as being a wire or tubular structure formed into a U-shaped or generally U-shaped configuration such that each loop has two opposing side segments 1772, 1774 with a bottom curved segment 1770. As will be understood by those of ordinary skill in the art, "side" and "bottom" are relative terms and utilized herein for illustration purposes only. The straight side segments may be parallel to each other, or may be slanted or angled away from each other as shown in FIG. 17 in which two straight slanted side segments 1772, 1774 flare apart as they extend from bottom curved segment 1770. As utilized herein, "generally" U-shaped includes wire or tubular structures formed into a horseshoe shape, a semi-circle, an oblong shape in which two parallel straight side segments have a generally straight bottom segment therebetween, and a V shape in which two straight slanted side segments are connected together by a curved apex. The loops may be considerably longer, shorter, wider, or narrower than shown. In any case, the loops are preferably configured to be a shape and size that can provide a positioning function and an anchoring function for valve prosthesis 1700 when the prosthesis is deployed at a native valve target site. For example, if valve prosthesis 1700 is positioned within the native aortic valve annulus, the loops extend from first or outflow end 216 of stent 202 and provide interference with the native valve leaflets and/or the walls of the native valve annulus, thereby inhibiting motion of valve prosthesis 1700 to achieve anchoring of the valve prosthesis. In addition, loops 1750 are positioned in the coronary cusps to provide anatomical and accurate positioning of transcatheter valve prosthesis 1700 prior to deployment of the transcatheter valve prosthesis. In particular, since self-expanding loops 1750 are positioned in the coronary cusps, centering mechanism 1720 provides both depth control as well as rotational alignment in order to properly position transcatheter valve prosthesis 1700.

Figure 18:
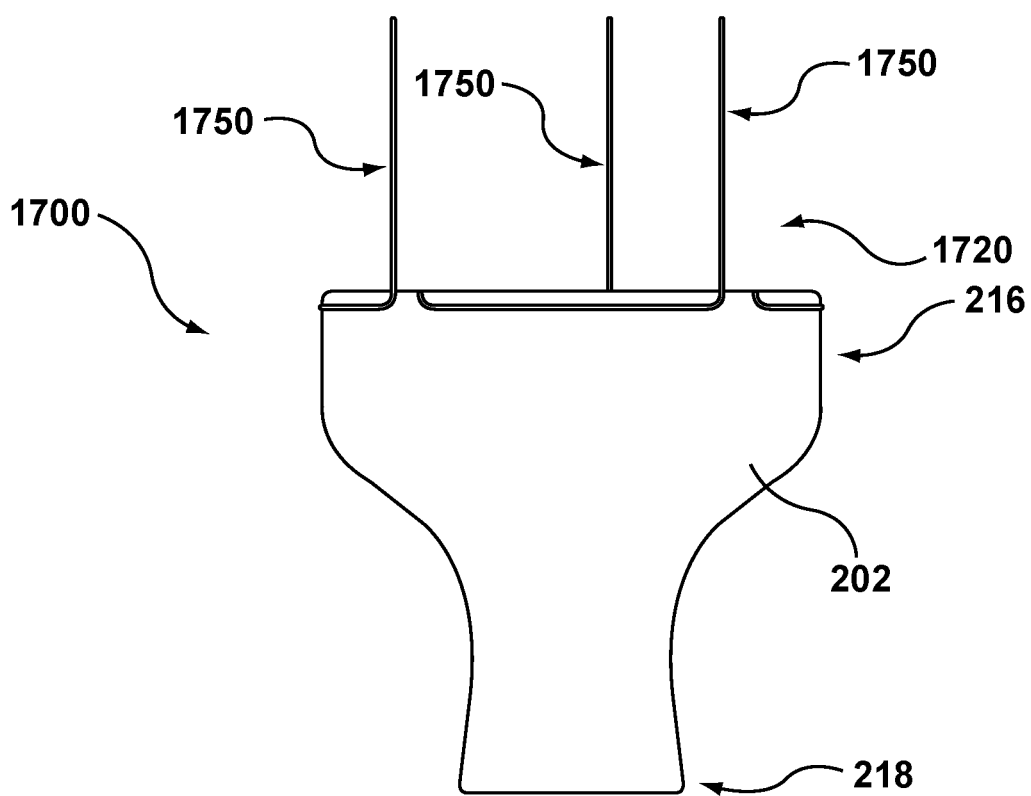
FIG. 18 is a side view illustration of the transcatheter valve prosthesis of FIG. 17, wherein the valve prosthesis and the centering mechanism are in compressed or delivery configurations.
Figure 19:
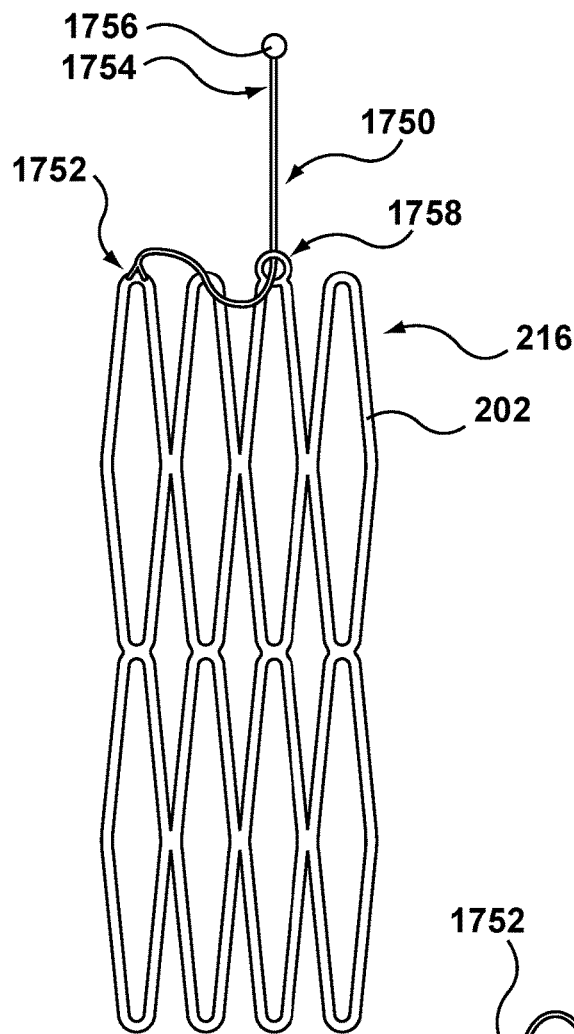
FIG. 19 is a side view of a portion of the transcatheter valve prosthesis of FIG. 17 laid flat for illustrative purposes only, wherein the stent and the loop thereof are in compressed or delivery configurations.
Figure 20:
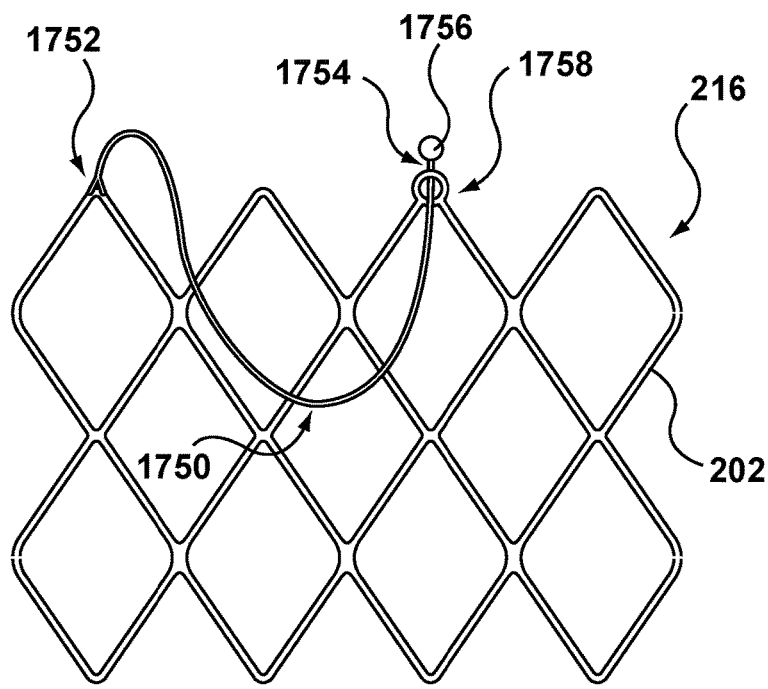
FIG. 20 is a side view of a portion of the transcatheter valve prosthesis of FIG. 17 laid flat for illustrative purposes only, wherein the stent and the loop thereof are in expanded or deployed configurations.

Deployment of loops 1750 will now be discussed in more detail with reference to FIG. 19 and FIG. 20. FIGS. 19 and 20 illustrate a portion of stent 202 laid flat for illustrative purposes, with a single loop 1750 coupled thereto. With reference to FIG. 18 and FIG. 19, in the compressed or delivery configuration, loop 1750 is approximately parallel with a longitudinal axis $L_a$ of stent 202 and proximally extends from first or outflow end 216 of stent 202. A first end 1752 is attached or fixed to first or outflow end 216 of stent 202 and a second end 1754 is slidingly coupled to first or outflow end 216 of stent 202 at a circumferentially spaced-apart location from first end 1752. More particularly, loop 1750 is threaded through an eyelet 1758 also attached or fixed to first or outflow end 216 of stent 202 such that second end 1754 is circumferentially spaced-apart from first or outflow end 216 of stent 202. A ball 1756 is attached to second end 1754 of loop 1750. Ball 1756 has a diameter greater than the opening defined by eyelet 1754 so that ball 1756 is sized to not pass through eyelet 1754. The addition of self-expanding loops 1750 to the profile of the delivery system is minimized because self-expanding loops 1750 are straightened and flush with the delivery system during delivery and also because self-expanding loops 1750 are positioned proximal to stent 202 rather than stacked or in parallel with the stent.

Each loop 1750 is formed from a self-expanding material such as Nitinol and shape-set in the deployed or expanded configuration shown in FIG. 17. Stated another way, the low energy configuration of each loop 1750 is the deployed or expanded configuration shown in FIG. 17. Balls 1756 may be utilized to straighten loops 1750 for delivery by pulling second ends 1754 into a delivery system. The delivery system retains loops in the delivery configuration until it is desired to deploy loops 1750. When loops 1750 are released from the delivery system, each loop 1750 is permitted to self-expand and resume its deployed or expanded configuration. With reference to FIG. 20, when loops 1750 self-expand, each loop 1750 slides through a respective eyelet 1756 and second ends 1754 of loops 1750 move towards first or outflow end 216 of stent 202 until balls 1756 contact or abut against eyelets 1758. As previously described, eyelets 1758 are sized to prevent second ends 1754 of loops 1750 from passing there-through.

Delivery and deployment of transcatheter valve prosthesis 1700 will now be described with reference to FIGS. 21-24. A valve delivery system 2130 having transcatheter valve prosthesis 1700 mounted thereon is percutaneously introduced into the vasculature, with transcatheter valve prosthesis 1700 in a delivery configuration. Valve delivery system 2130 utilizes multiple tubes or capsules to deploy centering mechanism 1720 and transcatheter valve prosthesis 1700. A first or proximal capsule or tube 2131 is proximally retracted in the ascending aorta during deployment to deploy centering mechanism 1720 and then a second or distal capsule or tube 2133 is distally advanced to deploy stent 202. For example, valve delivery system 2130 may be, but is not limited to, the delivery system which is utilized to deploy the ENGAGER device from Medtronic, Inc. of Minneapolis, Minnesota. Valve delivery system 2130 includes a distal tip 2134.

Figure 21:
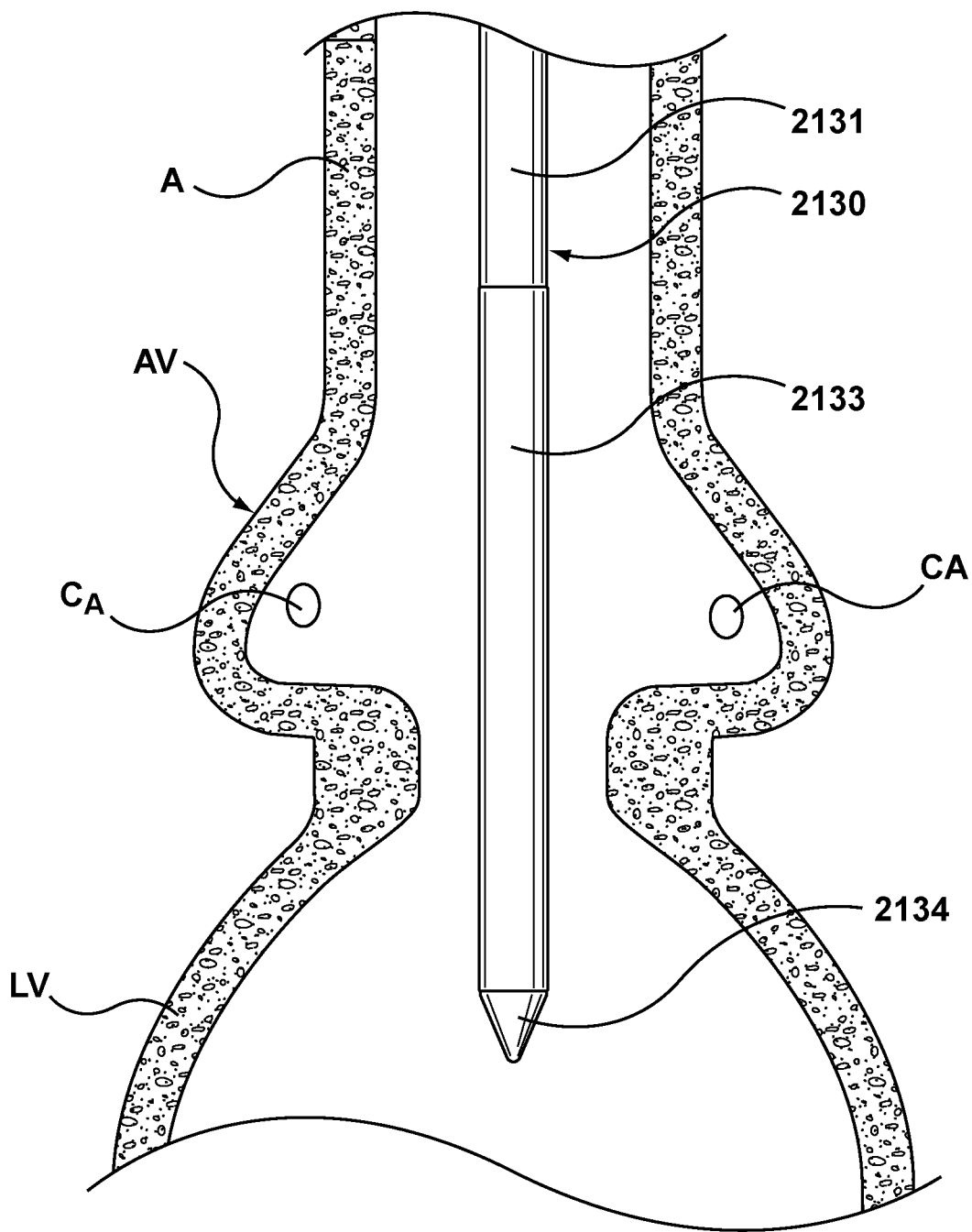
FIG. 21 is an illustration of the transcatheter valve prosthesis of FIG. 17 being delivered to a native aortic valve, wherein the valve prosthesis and the centering mechanism are compressed within a delivery system.

In the delivery configuration of FIG. 21, second or distal capsule 2133 is disposed over transcatheter valve prosthesis 1700 to compressively retain the transcatheter valve prosthesis in crimped engagement with the inner shaft (not shown) of the delivery system and first or proximal capsule 2131 is disposed over straightened loops 1750 to retain them in their delivery configuration. Valve delivery system 2130 is tracked through the vasculature until transcatheter valve prosthesis 1700 is positioned within the native valve annulus as shown in FIG. 21. Delivery of transcatheter valve prosthesis 1700 may be accomplished in accordance with techniques known in the field of interventional cardiology and/or interventional radiology. In an embodiment hereof, transcatheter valve prosthesis 1700 is configured for implantation in a target diseased native aortic valve AV that extends between a patient's left ventricle LV and a patient's aorta A. The coronary arteries $C_A$ are also shown on the sectional view of FIG. 21. Transcatheter valve prosthesis 1700 is configured for implantation via a percutaneous transfemoral approach and valve delivery system 2130 is transluminally advanced in a retrograde approach through the vasculature to the treatment site. More particularly, valve delivery system 2130 is tracked through the femoral artery, up the aorta and around the aortic arch in order to access the native aortic valve AV. Transcatheter valve prosthesis 1700 may also be positioned within the desired area of the heart via different delivery methods known in the art for accessing heart valves.

Figure 22:
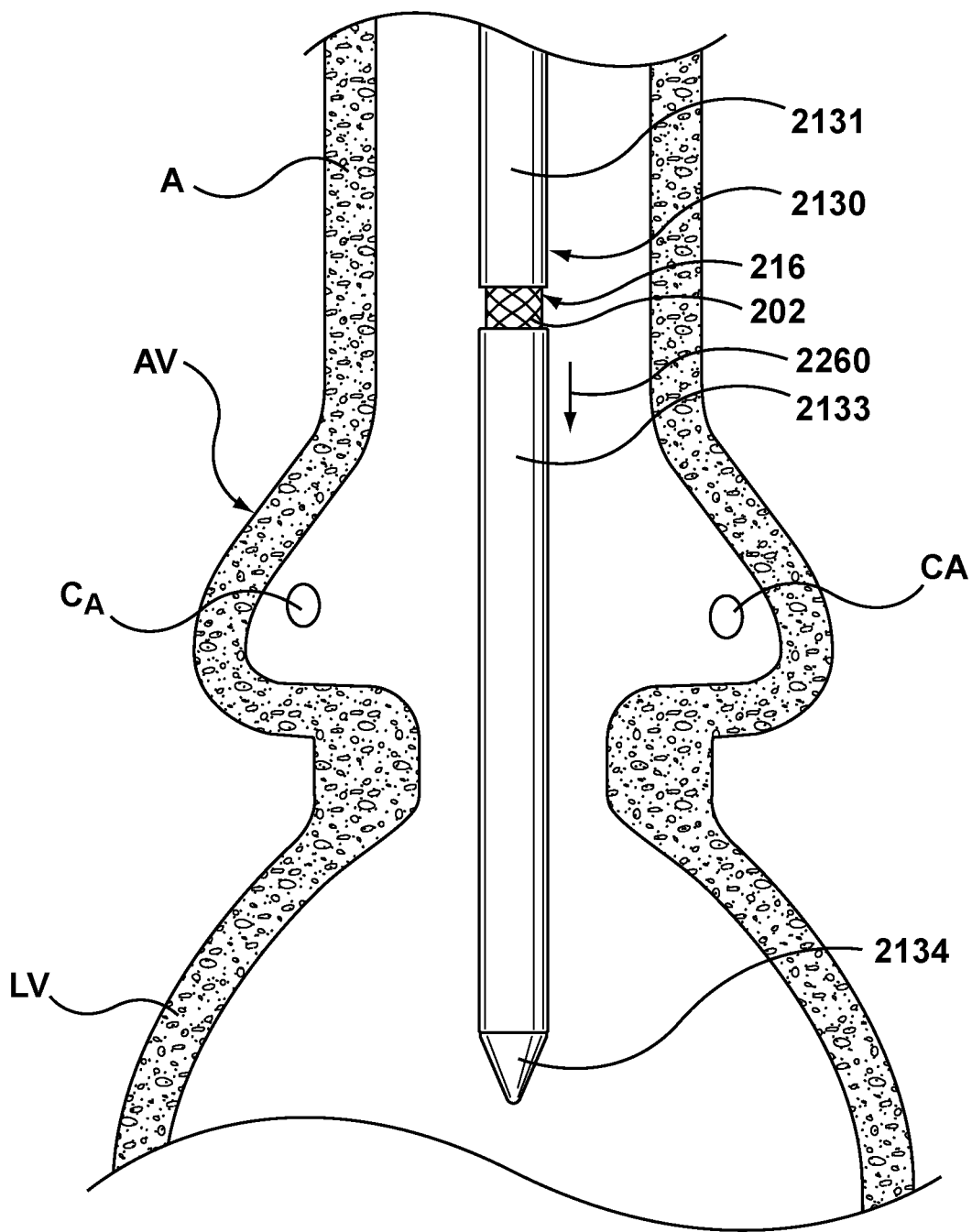
FIG. 22 is an illustration of the transcatheter valve prosthesis of FIG. 17 being deployed within a native aortic valve, wherein an outflow end of the valve prosthesis is partially deployed.

After transcatheter valve prosthesis 1700 is positioned within the native valve annulus as desired, second or distal capsule 2133 is slightly distally advanced as indicated by directional arrow 2260 in order to expose a short segment of first or outflow end 216 of tubular stent 202 as shown on FIG. 22. Next, first or proximal capsule 2131 is proximally retracted as indicated by directional arrow 2364 in order to deploy self-expanding loops 1750 as shown on FIG. 23. In addition or as an alternative to retracting proximal capsule 2131, loops 1750 may be pushed or distally advanced out of proximal capsule 2131 via a push rod (not shown) or similar mechanism built into the delivery system. When loops 1750 are released from proximal capsule 2131, each loop 1750 is permitted to self-expand and resume its deployed or expanded configuration as described above with respect to FIG. 20. At this stage of deployment, transcatheter valve prosthesis 1700 remains compressed within second or distal capsule 2133, except for a short segment at the outflow end 216 of stent 202 which is partially deployed.

Figure 23:
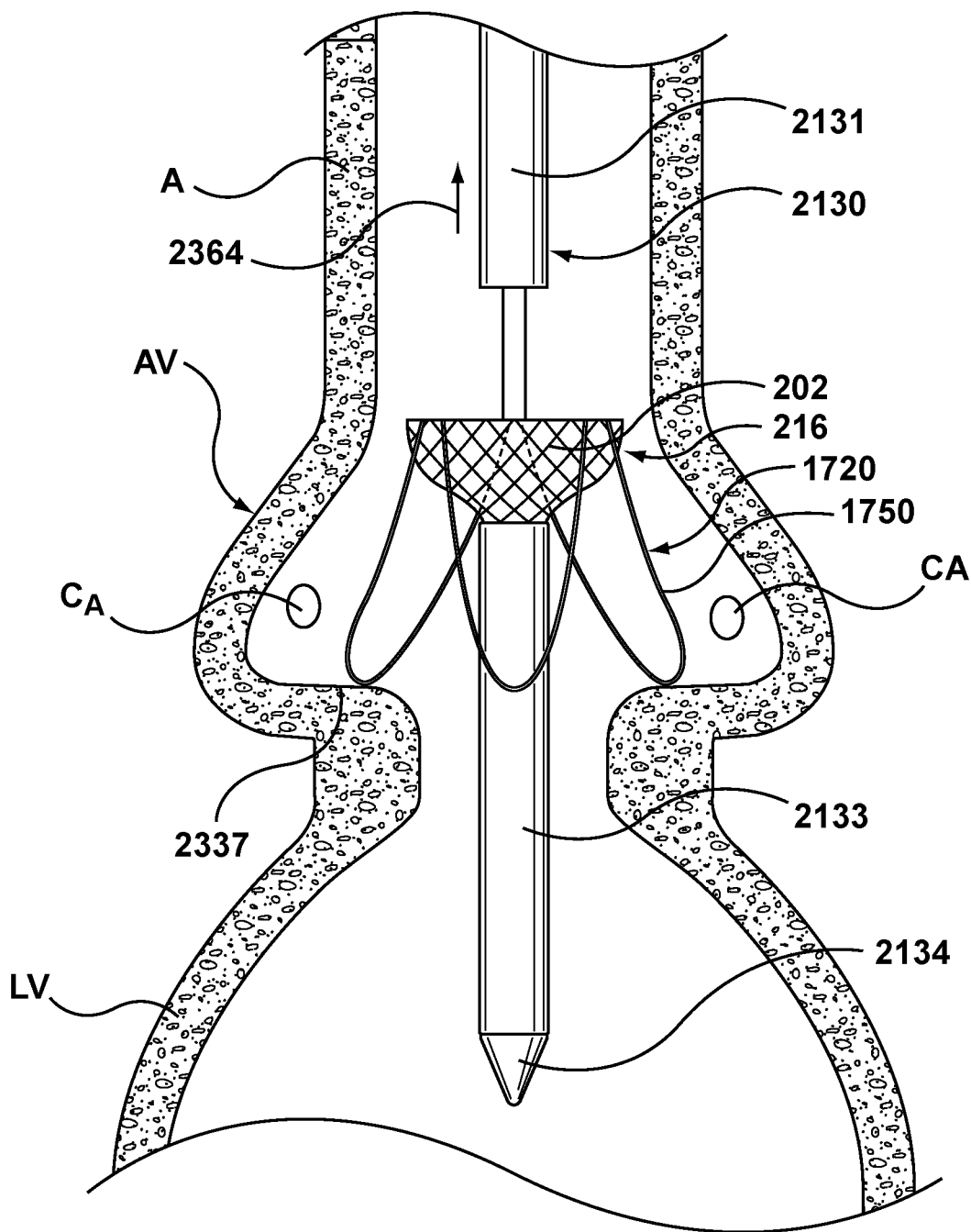
FIG. 23 is an illustration of the transcatheter valve prosthesis of FIG. 17 being deployed within a native aortic valve, wherein the centering mechanism is deployed and the outflow end of the valve prosthesis is partially deployed.

In FIG. 23, loops 1750 are shown deployed onto abutment surface 2337 of the native valve annulus. As such, loops 1750 are positioned in the coronary cusps and are utilized as depth markers or reference points to longitudinally center valve prosthesis 1700 by preventing the valve prosthesis from being positioned too deep or too shallow within the left ventricle LV. However, if loops 1750 deploy above abutment surface 2337 of the native valve annulus, valve delivery system 2130 may be manipulated in order to catch or contact deployed centering mechanism 1720 onto abutment surface 2337 of the native valve annulus. More particularly, valve delivery system 2130 may be distally advanced in order to translate or move valve prosthesis 1700 and centering mechanism 1720 until loops 1750 contact or abut against abutment surface 2337 of the native valve annulus as shown in FIG. 23.

Figure 24:
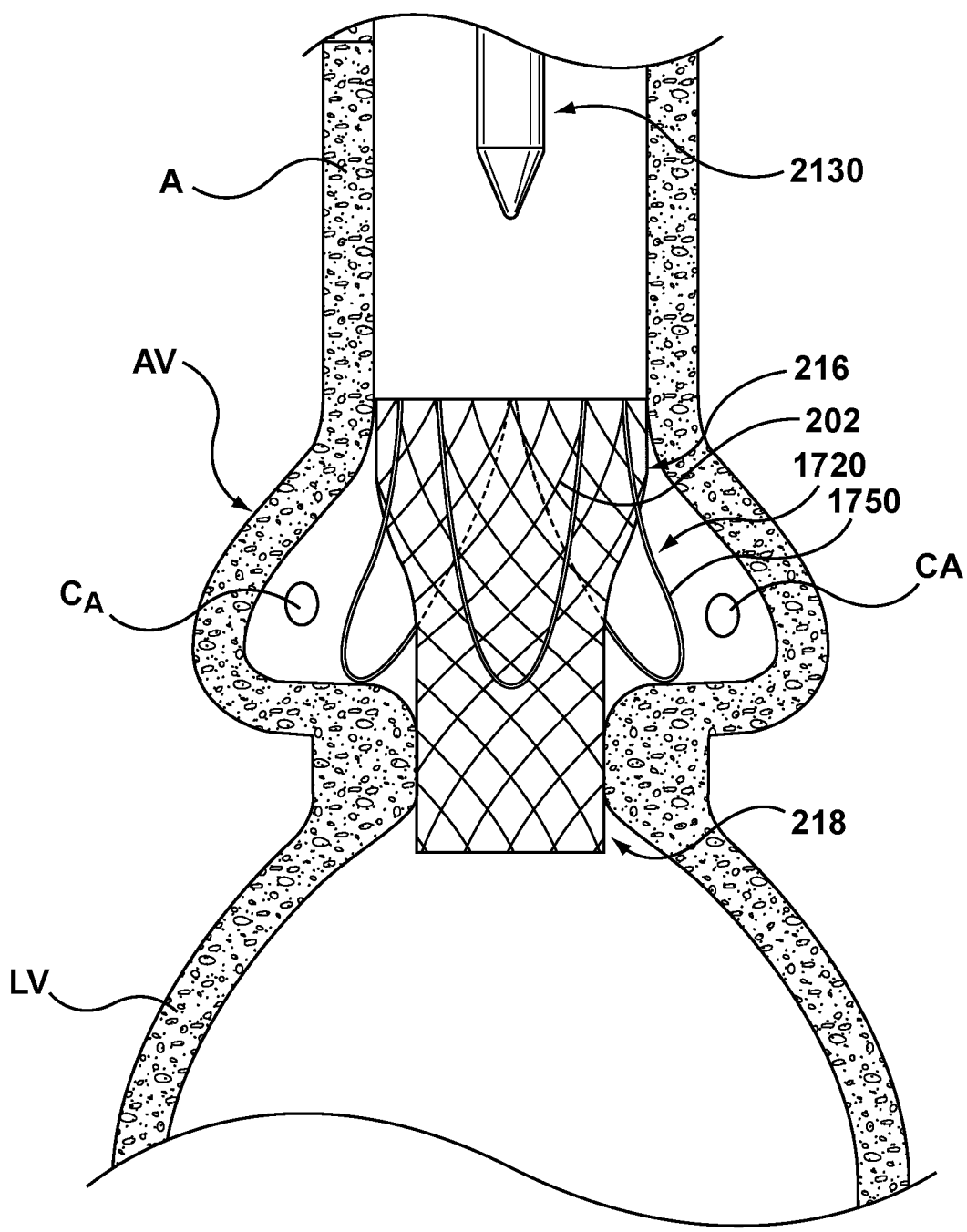
FIG. 24 is an illustration of the transcatheter valve prosthesis of FIG. 17 deployed within a native aortic valve, wherein the centering mechanism and the valve prosthesis are fully deployed.

Once loops 1750 are deployed and positioned as desired, valve prosthesis 1700 is then deployed into the expanded configuration via distal advancement of second or distal capsule 2133. Valve delivery catheter 2130 is then removed as shown in FIG. 24 and transcatheter valve prosthesis 1700 including integral centering mechanism 1720 remains deployed within the native target heart valve. Deployment of transcatheter valve prosthesis 1700 may thus be considered to occur via two consecutive stages with a first stage of deployment including deployment of centering mechanism 1720 and a second stage of deployment including deployment of tubular stent 202 having a prosthetic valve component therein.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising:
   a valve support frame having a compressed configuration for delivery within a vasculature and an expanded configuration for deployment within a native heart valve annulus, the valve support frame having an inflow end and an outflow end opposing the inflow end;
   a prosthetic valve component disposed within and secured to the valve support frame;
   a positioning component having a compressed configuration for delivery within a vasculature and an expanded configuration for deployment within a native heart valve, wherein the positioning component in each of the compressed configuration and the expanded configuration is coupled to and encircles an outer surface of the valve support frame and wherein the positioning component is coupled to an intermediate portion of the valve support frame extending between the inflow end and the outflow end of the valve support frame; and
   a flexible skirt attached to a surface of the positioning component,
   wherein the positioning component includes a ring and a plurality of spokes extending between the valve support frame and the ring, each spoke of the plurality of spokes having a first shape in the compressed configuration that is different from a second shape in the expanded configuration, and
   wherein the ring has an expanded diameter in the expanded configuration which is greater than an expanded diameter of the valve support frame in the expanded configuration.

2. The transcatheter valve prosthesis of claim 1, wherein the flexible skirt is formed from a low-porosity woven fabric or a pericardial tissue.

3. The transcatheter valve prosthesis of claim 1, wherein the ring is positioned radially spaced apart from an outer surface of the valve support frame when the valve support frame and the positioning component are both in their respective expanded configurations.

4. The transcatheter valve prosthesis of claim 1, wherein the flexible skirt is attached to an outer surface of the positioning component.

5. The transcatheter valve prosthesis of claim 1, wherein the ring and the plurality of spokes are formed from a self-expanding material.

6. The transcatheter valve prosthesis of claim 1, wherein the ring is a first ring and the positioning component includes a second ring attached to the valve support frame, the first ring disposed nearer to the inflow end of the valve support frame than the second ring, and the plurality of spokes extends between the first ring and the second ring.

7. The transcatheter valve prosthesis of claim 6, wherein a first end of each spoke of the plurality of spokes is attached to the first ring and a second end of each spoke of the plurality of spokes is attached to the second ring.

8. The transcatheter valve prosthesis of claim 6, wherein an open-ended annular pocket is formed between an inner surface of the flexible skirt and the outer surface of the valve support frame when the positioning component is in the expanded configuration.

9. The transcatheter valve prosthesis of claim 8, wherein the open-ended pocket forms a continuous circumferential seal around the valve support frame to block or prevent blood flow around a perimeter of the valve support frame, thereby minimizing or eliminating any paravalvular leakage after deployment.

10. A transcatheter valve prosthesis comprising:
a valve support frame having a compressed configuration for delivery within a vasculature and an expanded configuration for deployment within a native heart valve annulus, the valve support frame having an inflow end and an outflow end opposing the inflow end;
a prosthetic valve component disposed within and secured to the valve support frame;
a positioning component having a compressed configuration for delivery within a vasculature and an expanded configuration for deployment within a native heart valve, wherein the positioning component in each of the compressed configuration and the expanded configuration is coupled to and encircles an outer surface of the valve support frame and wherein the positioning component in the expanded configuration has a flat profile that extends transverse with respect to a longitudinal axis of the transcatheter valve prosthesis; and
a flexible skirt attached to a surface of the positioning component,
wherein the positioning component includes a ring and a plurality of spokes extending between the valve support frame and the ring, each spoke of the plurality of spokes having a first shape in the compressed configuration that is different from a second shape in the expanded configuration, and
wherein the ring has an expanded diameter in the expanded configuration which is greater than an expanded diameter of the valve support frame in the expanded configuration.

11. The transcatheter valve prosthesis of claim 10, wherein the spokes of the positioning component are formed from a strand of material that is woven between the valve support frame and the ring.

12. The transcatheter valve prosthesis of claim 11, wherein the strand of material is woven between cells formed within the valve support frame and loops around the ring.

13. The transcatheter valve prosthesis of claim 10, wherein each spoke of the plurality of spokes is substantially straight when the positioning component is in the expanded configuration.

14. The transcatheter valve prosthesis of claim 10, wherein each spoke of the plurality of spokes is a strand of material having a first end attached to the ring and a second end attached to the valve support frame.

15. A transcatheter valve prosthesis comprising:
a valve support frame having a compressed configuration for delivery within a vasculature and an expanded configuration for deployment within a native heart valve annulus, the valve support frame having an inflow end and an outflow end opposing the inflow end;
a prosthetic valve component disposed within and secured to the valve support frame; and
a positioning component having a compressed configuration for delivery within a vasculature and an expanded configuration for deployment within a native heart valve, wherein the positioning component in each of the compressed configuration and the expanded configuration is coupled to and encircles an outer surface of the valve support frame,
wherein the positioning component includes at least one self-expanding loop having a first shape in the compressed configuration that is different from a second shape in the expanded configuration, a first end of the at least one self-expanding loop being fixed to the valve support frame and a second end of the at least one self-expanding loop being slidingly coupled to the valve support frame,
wherein when the at least one self-expanding loop is in the compressed configuration the second end is longitudinally spaced apart from the first end and when the at least one self-expanding loop is in the expanded configuration the second end is circumferentially spaced apart from the second end of the loop.

16. The transcatheter valve prosthesis of claim 15, wherein the positioning component is attached to the outflow end of the valve support frame.

17. The transcatheter valve prosthesis of claim 16, wherein when the at least one self-expanding loop is in the compressed configuration the loop has a straightened profile with the second end being longitudinally spaced apart from the outflow end of the valve support frame and when the at least one self-expanding loop is in the expanded configuration the loop has a U-shaped profile with the second end being disposed adjacent to the outflow end of the valve support frame.

18. The transcatheter valve prosthesis of claim 15, wherein the at least one self-expanding loop includes three self-expanding loops.

19. The transcatheter valve prosthesis of claim 15, wherein the at least one self-expanding loop includes an elongated body, the second end of the at least one self-expanding loop having a diameter that is greater than a diameter of the elongated body, and wherein the valve support frame includes a central opening sized to permit passage of the elongated body of the at least one self-expanding loop but not permit passage of the second end of the at least one self-expanding loop.

* * * * *